United States Patent
Ando et al.

(10) Patent No.: US 11,844,822 B2
(45) Date of Patent: Dec. 19, 2023

(54) SOLID FORMULATION AND METHOD FOR PREVENTING OR REDUCING COLORATION THEREOF

(71) Applicant: Elobix AB, Gothenburg (SE)

(72) Inventors: Takahiko Ando, Kawasaki (JP); Hirokazu Hagio, Kawasaki (JP); Takashi Matsushita, Kawasaki (JP); Yusuke Ito, Kawasaki (JP)

(73) Assignee: Elobix AB, Gothenburg (SE)

( * ) Notice: Subject to any disclaimer, the term of this patent is extended or adjusted under 35 U.S.C. 154(b) by 458 days.

(21) Appl. No.: 16/901,800

(22) Filed: Jun. 15, 2020

(65) Prior Publication Data

US 2020/0376071 A1   Dec. 3, 2020

Related U.S. Application Data

(63) Continuation of application No. 15/320,621, filed as application No. PCT/JP2015/068242 on Jun. 24, 2015, now Pat. No. 10,709,755.

(30) Foreign Application Priority Data

Jun. 25, 2014 (JP) ................ 2014-130092

(51) Int. Cl.
*A61K 31/554* (2006.01)
*A61K 38/05* (2006.01)
*A61K 9/28* (2006.01)
*A61K 9/20* (2006.01)

(52) U.S. Cl.
CPC ............ *A61K 38/05* (2013.01); *A61K 9/2009* (2013.01); *A61K 9/2018* (2013.01); *A61K 9/2054* (2013.01); *A61K 9/2068* (2013.01); *A61K 9/284* (2013.01); *A61K 9/2853* (2013.01); *A61K 9/2866* (2013.01); *A61K 31/554* (2013.01)

(58) Field of Classification Search
CPC ..... A61K 38/05; A61K 31/554; A61K 9/2009
See application file for complete search history.

(56) References Cited

U.S. PATENT DOCUMENTS

| | | | |
|---|---|---|---|
| 3,539,380 A | 11/1970 | Johnson | |
| 4,172,120 A | 10/1979 | Todd et al. | |
| 4,507,235 A | 3/1985 | Wunsch | |
| 5,049,394 A | 9/1991 | Howard et al. | |
| 5,167,965 A | 12/1992 | Schulz | |
| 5,294,448 A | 3/1994 | Ring | |
| 5,384,130 A | 1/1995 | Kamada | |
| 5,422,124 A | 6/1995 | Valducci | |
| 5,578,316 A | 11/1996 | Bhardwaj et al. | |
| 5,681,584 A | 10/1997 | Savastano | |
| 5,811,388 A | 9/1998 | Friend et al. | |
| 5,900,233 A | 5/1999 | Day | |
| 5,976,811 A | 11/1999 | Mullner et al. | |
| 5,994,391 A | 11/1999 | Lee et al. | |
| 6,069,167 A | 5/2000 | Sokol | |
| 6,277,831 B1 | 8/2001 | Frick et al. | |
| 6,346,527 B1 | 2/2002 | Takanaka et al. | |
| 6,355,672 B1 | 3/2002 | Yasuma et al. | |
| 6,387,924 B2 | 5/2002 | Lee et al. | |
| 6,387,944 B1 | 5/2002 | Frick et al. | |
| 6,426,340 B1 | 7/2002 | Gibson et al. | |
| 6,592,900 B1 | 7/2003 | Buhler | |
| 6,635,280 B2 * | 10/2003 | Shell .................... | A61K 9/2054 424/464 |
| 6,676,979 B2 | 1/2004 | Marlett et al. | |
| 6,906,058 B2 | 6/2005 | Starke et al. | |
| 6,943,189 B2 | 9/2005 | Keller et al. | |
| 7,019,023 B2 | 3/2006 | Frick et al. | |
| 7,125,864 B2 | 10/2006 | Starke et al. | |
| 7,132,416 B2 | 11/2006 | Starke et al. | |
| 7,132,557 B2 | 11/2006 | Wilkes et al. | |
| 7,192,945 B2 | 3/2007 | Starke et al. | |
| 7,192,946 B2 | 3/2007 | Starke et al. | |
| 7,192,947 B2 | 3/2007 | Starke et al. | |
| 7,226,943 B2 | 6/2007 | Starke et al. | |
| 7,238,684 B2 | 7/2007 | Starke et al. | |
| 7,514,421 B2 | 4/2009 | Abrahamsson et al. | |
| 7,767,229 B1 | 8/2010 | Milne et al. | |

(Continued)

FOREIGN PATENT DOCUMENTS

| CA | 2065151 | 3/1991 |
|---|---|---|
| CN | 102525943 | 7/2012 |

(Continued)

OTHER PUBLICATIONS

No Author Listed],"Practical Pharmaceutical Preparation Technology", People's Medical Publishing House, Jan. 1999, 286-287 (Machine Translation).

A Long-Term, Open-Label Study of LUM001 With a Double-Blind, Placebo Controlled, Randomized Drug Withdrawal Period to Evaluate Safety and Efficacy in Children With Alagille Syndrome (ICONIC), Clinical Trials.gov, Jun. 9, 2014, retrieved Oct. 3, 2014, http://clinicaltrials.gov/ct2/show/NCT02160782?term=LUM001&rank=7, 4 pages.

AASLD: 2017 68th Annual Meeting of the American Association for the Study of Liver Diseases, Washington, DC, Oct. 20-24, 2017, (Abstract only).

Adams et al., "Hepascore: an accurate validated predictor of liver fibrosis in chronic hepatitis C infection," Clin. Chem. 2005, vol. 51(10), p. 1867-1873.

(Continued)

*Primary Examiner* — John S Kenyon
(74) *Attorney, Agent, or Firm* — Fish & Richardson P.C.

(57) ABSTRACT

The present invention relates to stabilization of a certain benzothia(dia)zepine derivative in a solid formulation containing the same. In the present invention, in a solid formulation containing the benzothia(dia)zepine derivative mentioned above, a combination of polyethylene glycol and polyvinyl alcohol is not blended, or alternatively, in the case of blending polyethylene glycol and polyvinyl alcohol in the solid formulation, the aforementioned derivative is isolated from the combination of polyethylene glycol and polyvinyl alcohol.

20 Claims, No Drawings

(56) References Cited

U.S. PATENT DOCUMENTS

| | | | |
|---|---|---|---|
| 7,923,468 B2 | 4/2011 | Frick et al. | |
| 7,939,061 B2 | 5/2011 | Prakash et al. | |
| 8,048,413 B2 | 11/2011 | Huguet | |
| 8,067,584 B2 | 11/2011 | Starke et al. | |
| 9,023,368 B2 | 5/2015 | Basit et al. | |
| 9,295,677 B2 | 3/2016 | Ling et al. | |
| 9,684,018 B2 | 6/2017 | Horanzy | |
| 9,694,018 B1 | 7/2017 | Gillberg et al. | |
| 9,701,649 B2 | 7/2017 | Bohlin et al. | |
| 9,745,276 B2 | 8/2017 | Bohlin et al. | |
| 9,872,844 B2 | 1/2018 | Zernel et al. | |
| 10,093,697 B2 | 10/2018 | Gillberg et al. | |
| 10,183,920 B2 | 1/2019 | Ymen et al. | |
| 10,487,111 B2 | 11/2019 | Gillberg et al. | |
| 10,610,543 B2 | 4/2020 | Gillberg et al. | |
| 10,709,755 B2 * | 7/2020 | Ando | A61P 3/10 |
| 10,786,529 B2 | 9/2020 | Gillberg et al. | |
| 10,793,534 B2 | 10/2020 | Gillberg | |
| 10,799,527 B2 | 10/2020 | Gillberg et al. | |
| 10,864,228 B2 | 12/2020 | Gilberg et al. | |
| 10,881,685 B2 | 1/2021 | Gillberg et al. | |
| 10,941,127 B2 | 3/2021 | Gilberg et al. | |
| 10,975,045 B2 | 4/2021 | Gillberg et al. | |
| 10,975,046 B2 | 4/2021 | Lundqvist et al. | |
| 10,981,952 B2 | 4/2021 | Gilberg et al. | |
| 10,995,115 B2 | 5/2021 | Bhat et al. | |
| 11,007,142 B2 | 5/2021 | Gillberg et al. | |
| 11,014,898 B1 | 5/2021 | Gillberg et al. | |
| 11,111,224 B2 | 9/2021 | Gillberg | |
| 11,180,465 B2 | 11/2021 | Gillberg et al. | |
| 11,225,466 B2 | 1/2022 | Gillberg et al. | |
| 11,261,212 B2 | 3/2022 | Gillberg et al. | |
| 11,267,794 B2 | 3/2022 | Gillberg et al. | |
| 11,306,064 B2 | 4/2022 | Gillberg et al. | |
| 11,572,350 B1 | 2/2023 | Gillberg et al. | |
| 2002/0054903 A1 | 5/2002 | Tyler et al. | |
| 2003/0124088 A1 | 7/2003 | Masuda et al. | |
| 2003/0125316 A1 | 7/2003 | Keller et al. | |
| 2003/0143183 A1 | 7/2003 | Knudsen et al. | |
| 2003/0153541 A1 | 8/2003 | Dudley et al. | |
| 2003/0153607 A1 | 8/2003 | Glinecke | |
| 2003/0215843 A1 | 11/2003 | Poupon et al. | |
| 2004/0014806 A1 | 1/2004 | Bhat et al. | |
| 2004/0038862 A1 | 2/2004 | Goodwin et al. | |
| 2004/0062745 A1 | 4/2004 | Green et al. | |
| 2004/0077625 A1 | 4/2004 | Tremont et al. | |
| 2004/0082647 A1 | 4/2004 | Babiak et al. | |
| 2004/0176438 A1 | 9/2004 | Tremont et al. | |
| 2005/0009805 A1 | 1/2005 | Sasahara et al. | |
| 2005/0089572 A1 | 4/2005 | Kumar | |
| 2005/0113362 A1 | 5/2005 | Lindstedt et al. | |
| 2005/0118326 A1 | 6/2005 | Anfinsen | |
| 2005/0124557 A1 | 6/2005 | Lindqvist | |
| 2005/0171204 A1 | 8/2005 | Lindstedt et al. | |
| 2005/0197376 A1 | 9/2005 | Kayakiri et al. | |
| 2005/0215882 A1 | 9/2005 | Chenevert et al. | |
| 2005/0266080 A1 | 12/2005 | Desai et al. | |
| 2005/0282822 A1 | 12/2005 | Alstermark et al. | |
| 2005/0287178 A1 | 12/2005 | Steed | |
| 2006/0083790 A1 | 4/2006 | Anderberg et al. | |
| 2006/0210631 A1 | 9/2006 | Patel | |
| 2006/0210633 A1 | 9/2006 | Dharmadhikari | |
| 2007/0197522 A1 | 8/2007 | Edwards et al. | |
| 2007/0237818 A1 | 10/2007 | Malcom et al. | |
| 2008/0193543 A1 | 8/2008 | Morello | |
| 2008/0207592 A1 | 8/2008 | Frick et al. | |
| 2008/0300171 A1 | 12/2008 | Balkan et al. | |
| 2009/0098200 A1 | 4/2009 | Temtsin Krayz et al. | |
| 2009/0131395 A1 | 5/2009 | Antonelli et al. | |
| 2010/0130472 A1 | 5/2010 | Young et al. | |
| 2010/0286122 A1 | 11/2010 | Belyk | |
| 2010/0316722 A1 | 12/2010 | Lopez-Belmonte Encina et al. | |
| 2011/0003782 A1 | 1/2011 | Pellicciari | |
| 2011/0152204 A1 | 6/2011 | Gedulin et al. | |
| 2011/0159087 A1 | 6/2011 | Sathe et al. | |
| 2011/0294767 A1 | 12/2011 | Gedulin et al. | |
| 2012/0114588 A1 * | 5/2012 | Starke | A61P 3/04 540/545 |
| 2013/0029938 A1 | 1/2013 | Aquino et al. | |
| 2013/0052269 A1 | 2/2013 | Lescure | |
| 2013/0059807 A1 | 3/2013 | Gedulin et al. | |
| 2013/0108573 A1 | 5/2013 | Gedulin et al. | |
| 2013/0109671 A1 | 5/2013 | Gedulin et al. | |
| 2013/0225511 A1 | 8/2013 | Gillberg et al. | |
| 2013/0236541 A1 | 9/2013 | Gillberg et al. | |
| 2014/0275090 A1 | 9/2014 | Gedulin et al. | |
| 2015/0031637 A1 | 1/2015 | Gillberg et al. | |
| 2016/0146715 A1 | 5/2016 | Shim et al. | |
| 2017/0143738 A1 | 5/2017 | Ando et al. | |
| 2017/0182059 A1 | 6/2017 | Gillberg et al. | |
| 2017/0182115 A1 | 6/2017 | Gillberg et al. | |
| 2017/0224721 A1 | 8/2017 | Gillberg et al. | |
| 2017/0240516 A1 | 8/2017 | Ymen et al. | |
| 2018/0140219 A1 | 5/2018 | Yin et al. | |
| 2018/0264030 A1 | 9/2018 | Gillberg et al. | |
| 2018/0362577 A1 | 12/2018 | Gillberg et al. | |
| 2019/0046451 A1 | 2/2019 | Gillberg et al. | |
| 2019/0070217 A1 | 3/2019 | Gillberg et al. | |
| 2019/0367467 A1 | 12/2019 | Gillberg et al. | |
| 2020/0002299 A1 | 1/2020 | Lundqvist | |
| 2020/0046635 A1 | 2/2020 | Gillberg et al. | |
| 2020/0046636 A1 | 2/2020 | Gillberg et al. | |
| 2020/0046757 A1 | 2/2020 | Gillberg et al. | |
| 2020/0046758 A1 | 2/2020 | Gillberg et al. | |
| 2020/0049611 A1 | 2/2020 | Gillberg et al. | |
| 2020/0140484 A1 | 5/2020 | Gillberg et al. | |
| 2020/0247769 A1 | 8/2020 | Gillberg et al. | |
| 2021/0017141 A1 | 1/2021 | Gillberg et al. | |
| 2021/0147372 A1 | 5/2021 | Gillberg | |
| 2021/0171479 A1 | 6/2021 | Gillberg | |
| 2021/0171480 A1 | 6/2021 | Gillberg | |
| 2021/0171481 A1 | 6/2021 | Gillberg | |
| 2021/0171482 A1 | 6/2021 | Gillberg | |
| 2021/0171483 A1 | 6/2021 | Gillberg | |
| 2021/0177767 A1 | 6/2021 | Byrod | |
| 2021/0179572 A1 | 6/2021 | Gillberg | |
| 2021/0236511 A1 | 8/2021 | Byrod | |
| 2021/0340175 A1 | 11/2021 | Gillberg | |
| 2021/0387956 A1 | 12/2021 | Gillberg | |
| 2022/0041567 A1 | 2/2022 | Gillberg et al. | |
| 2022/0143043 A1 | 5/2022 | Gillberg | |
| 2022/0402885 A1 | 12/2022 | Gillberg et al. | |
| 2023/0049950 A1 | 2/2023 | Gillberg et al. | |
| 2023/0109432 A1 | 4/2023 | Gillberg et al. | |

FOREIGN PATENT DOCUMENTS

| | | |
|---|---|---|
| DE | 3930168 | 3/1991 |
| DE | 19825804 | 8/2000 |
| EP | 0278464 | 8/1988 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0594570 | 7/1995 |
| EP | 0864582 | 9/1998 |
| EP | 1173205 | 4/2000 |
| EP | 1045840 | 10/2000 |
| EP | 1273307 | 1/2003 |
| EP | 1535913 | 6/2005 |
| EP | 1719768 | 11/2006 |
| EP | 2144599 | 2/2008 |
| EP | 3210977 | 8/2017 |
| GB | 1573487 | 8/1980 |
| GB | 2262888 | 7/1996 |
| JP | 2000-513028 | 10/2000 |
| JP | B-3665055 | 6/2005 |
| JP | 2006/124695 | 5/2006 |
| JP | B-4870552 | 2/2012 |
| JP | 2013-541584 | 11/2013 |

(56) References Cited

FOREIGN PATENT DOCUMENTS

| | | |
|---|---|---|
| JP | A-2013-542953 | 11/2013 |
| JP | B-5421326 | 2/2014 |
| RU | 2314104 | 1/2008 |
| WO | WO 1991/03249 | 3/1991 |
| WO | WO 1993/16055 | 8/1993 |
| WO | WO 1994/00111 | 1/1994 |
| WO | WO 1994/18183 | 8/1994 |
| WO | WO 1994/18184 | 8/1994 |
| WO | WO 1996/05188 | 2/1996 |
| WO | WO 1996/08484 | 3/1996 |
| WO | WO 1996/16051 | 5/1996 |
| WO | WO 1997/33882 | 9/1997 |
| WO | WO 1998/03818 | 1/1998 |
| WO | WO 1998/07449 | 1/1998 |
| WO | WO 1998/38182 | 9/1998 |
| WO | WO 1998/40375 | 9/1998 |
| WO | WO 1998/56757 | 12/1998 |
| WO | WO 1999/01149 | 1/1999 |
| WO | WO 1999/32478 | 7/1999 |
| WO | WO 1999/35135 | 7/1999 |
| WO | WO 1999/64409 | 7/1999 |
| WO | WO 1999/64410 | 12/1999 |
| WO | WO 2000/01687 | 1/2000 |
| WO | WO 2000/38725 | 7/2000 |
| WO | WO 2000/38726 | 7/2000 |
| WO | WO 2000/38727 | 7/2000 |
| WO | WO 2000/38728 | 7/2000 |
| WO | WO 2000/38729 | 7/2000 |
| WO | WO 2000/47568 | 8/2000 |
| WO | WO 2000/61568 | 10/2000 |
| WO | WO 2000/62810 | 10/2000 |
| WO | WO 2001/34570 | 5/2001 |
| WO | WO 2001/60807 | 8/2001 |
| WO | WO 2001/66533 | 9/2001 |
| WO | WO 2001/68096 | 9/2001 |
| WO | WO 2001/68637 | 9/2001 |
| WO | WO 2002/08211 | 1/2002 |
| WO | WO 2002/09815 | 4/2002 |
| WO | WO 2002/32428 | 4/2002 |
| WO | WO 2002/53548 | 6/2002 |
| WO | WO 2003/020710 | 3/2003 |
| WO | WO 2003/022286 | 3/2003 |
| WO | WO 2003/022804 | 3/2003 |
| WO | WO 2003/022825 | 3/2003 |
| WO | WO 2003/022830 | 3/2003 |
| WO | WO 2003/043992 | 5/2003 |
| WO | WO 2003/051821 | 6/2003 |
| WO | WO 2003/051822 | 6/2003 |
| WO | WO 2003/061663 | 7/2003 |
| WO | WO 2003/091232 | 11/2003 |
| WO | WO 2003/106482 | 12/2003 |
| WO | WO 2004/006899 | 1/2004 |
| WO | WO 2004/056748 | 7/2004 |
| WO | WO 2004/076430 | 9/2004 |
| WO | WO 2004/020421 | 10/2004 |
| WO | WO 2004/089350 | 10/2004 |
| WO | WO 2005/082874 | 9/2005 |
| WO | WO 2007/009655 | 1/2007 |
| WO | WO 2007/009656 | 1/2007 |
| WO | WO 2008/058628 | 5/2008 |
| WO | WO 2008/058630 | 5/2008 |
| WO | WO 2008/058631 | 5/2008 |
| WO | WO 2011/137135 | 11/2011 |
| WO | WO 2012/064267 | 5/2012 |
| WO | WO 2012/064268 | 5/2012 |
| WO | WO 2013/063512 | 5/2013 |
| WO | WO 2013/063526 | 5/2013 |
| WO | WO 2013/168671 | 11/2013 |
| WO | WO 2014/174066 | 10/2014 |
| WO | WO 2014/179453 | 11/2014 |
| WO | WO 2015/193788 | 12/2015 |
| WO | WO 2017/138876 | 8/2017 |
| WO | WO 2017/138877 | 8/2017 |
| WO | WO 2017/138878 | 8/2017 |
| WO | WO 2019/172834 | 9/2019 |
| WO | WO 2019/234077 | 12/2019 |
| WO | WO 2019/245448 | 12/2019 |
| WO | WO 2019/245449 | 12/2019 |
| WO | WO 2020/161216 | 8/2020 |
| WO | WO 2020/161217 | 8/2020 |
| WO | WO 2020/167958 | 8/2020 |
| WO | WO 2020/167964 | 8/2020 |
| WO | WO 2020/167981 | 8/2020 |

OTHER PUBLICATIONS

Alagile Syndrome,Wikipedia, the free encyclopedia, posted on or about Feb. 11, 2005, retrieved Feb. 12, 2014, http://en.wikipedia.org/wiki/Alagille_syndrome, 3 pages.

Alashkar et al., "Meeting Info.: 57th Annual Meeting of the AmericanSociety-of-Hematology," Orlando, FL, USA. Dec. 5-8, 2015, Amer Soc Hematol, Blood, 2015, 126(23).

Albireo's Lead Compound in Cholestatic Liver Diseases, A4250, Projects Against Bile Acid-Mediated Cholestatic Liver Injury in Mice, Albireo Press Release, Apr. 11, 2014, 2 pages.

Alissa et al., "Invited Review: Update on Progressive Familial Intrahepatic Cholestasis," Journal of Pediatric Gastroenterology and Nutrition, 2008, 46:241-252.

Allison et al., "Studies on mixed populations of human intestinal bacteria grown in single-stage and multistage continuous culture systems," Appl. Environ. Microbial. 1989, 55(3):672-678.

Alnouti, "Bile acid sulfation: a pathway of bile acid elimination and detoxification," Toxicological Sciences, 2009, 108(2):225-246.

Alonso et al., "Histologic pathology of the liver in progressive familial intrahepatic cholestasis," Journal of Pediatric Gastroenterology and Nutrition, 14: 128-133, 1994.

Alvarez et al., "Reduced hepatic expression of farnesoid X receptor in hereditary cholestasis associated to mutation in ATP8B1," Hum Mol Genet, 2004, 13(20):2451-2460.

Alvarez, "Development of crystallization processes for pharmaceutical applications," LACCEI, 2007, 2E.3-1-2E.3-9.

Alvarez, Fernando; "Treatments in chronic cholestasis in children." Ann. Nestlé (2008) 66 p. 127-135.

American Diabetes Association, "Management of Dyslipidemia in Adults with Diabetes," Diabetes Care, Jan. 2003, 26(1).

An Extension Study to Evaluate the Long-Term Safety and Durability of Effect of LUM001 in the Treatment of Cholestatic Liver Disease in Subjects With Alagille Syndrome (IMAGINE), Clinical Trials.gov, Jan. 23, 2014, retrieved on Oct. 3, 2014, http://clinicaltrials.gov/ct2/show/NCT02047318?term=LUM001&rank=3, 3 pages.

An Extension Study to Evaluate the Long-Term Safety and Durability of Effect of LUM001 in the Treatment of Cholestatic Liver Disease in Subjects With Alagille Syndrome (IMAGINE-II), Clincal Trials.gov, Apr. 16, 2014, retrieved on Oct. 3, 2014, http://clinicaltrials.gov/ct2/show/NCT02117713?term=LUM001&rank=2, 3 pages.

Anakk et al., "Bile acids activate YAP to promote liver carcinogenesis," Cell Rep., Nov. 27, 2013, 5(4):1060-1069.

Angulo et al., "Independent Predictors of Liver Fibrosis in Patients With Nonalcoholic Steatohepatitis," Hepatology, Dec. 1999, 30(6): 1356-1362.

Angulo et al., "The NAFLD fibrosis score: a noninvasive system that identifies liver fibrosis in patients with NAFLD," Hepatology, 2007, vol. 45(4), p. 846-854.

Angulo, "Use of ursodeoxycholic acid in patients with liver disease," Current Gastroenterology Reports, Feb. 1, 2002, 4(1):37-44.

Anzivino et al., "ABCB4 and ABCB11 mutations in intrahepatic cholestasis of pregnancy in an Italian population," Dig Liver Dis., 2013, 45(3):226-232.

Appleby et al., "Effects of conventional and a novel colonic-release bile acid sequestrant, A3384, on fibroblast growth factor 19 and bile acid metabolism in healthy volunteers and patients with bile acid diarrhoea", United Eur. Gastroent. J., vol. 5, pp. 380-388, 2017.

Arnell et al., "Follow-up in children with progressive familial intrahepatic cholestasis after partial external biliary diversion," J Pediatr Gastroenterol Nutr., 2010, 51(4):494-499.

Artursson and Karlsson, "Correlation Between Oral Drug Absorption in Humans and Apparent Drug Permeability Coefficients in

(56) References Cited

OTHER PUBLICATIONS

Human Intestinal Epithelial (CACO-2) Cells," Biochemical and Biophysical Research Communications, Mar. 1991, 175(3):880-885.
Attili et al., "Bile Acid-induced Liver Toxicity: Relation to the Hydrophobic-Hydrophilic Balance of Bile Acids," Medical Hypotheses, 1986, 19:57-69.
Baghdasaryan et al., "Inhibition of intestinal bile acid absorption by ASBT inhibito A4250 protects against bile acid-mediated cholestatic liver injury in mice," J. Hepatology, 2014, 60:S57.
Baghdasaryan et al., "Inhibition of intestinal bile acid absorption by ASBT inhibitor A4250 protects against bile acid-mediated cholestatic liver injury in mice," Presented at the EASL Conference, London, UK, Apr. 12, 2015, http://www.albireopharma.com/News.aspx?PageID=1591817, 22 pages.
Bajor et al., "Bile acids: short and long term effects in the intestine," Scandanavian J. Gastro., 2010, 45:645-664.
Balbach et al., "Pharmaceutical evaluation of early development candidates "the 100 mg-approach"," Int J Pharm, May 4, 2004, 275(1):1-12.
Banker et al., "Modern Pharmaceutics, 3ed", Marcel Dekker, New York, 1996, pp. 451 and 596.
Baumann, U. et al., "The ileal bile acid transport inhibitor A4250 decreases pruritus and serum bile acids in cholestatic liver diseases—an ongoing multiple dose, open-label, multicenter study," Hepatology, 2017, 66(1): S91 (Abstract only).
Bavin, "Polymorphism in Process Development," Chemistry and Industry, 527-529, 1989.
Beausejour et al., "Description of two new ABCB11 mutations responsible for type 2 benign recurrent intrahepatic cholestasis in a French-Canadian family," Can J Gastroenterol., 2011, 25(6):311-314.
Beraza et al., Nor-ursodeoxycholic acid reverses hepatocyte-specific nemo-dependnt steatohepatitis. Gut, 2011: 60: 387-396.
Bhaskaran et al., "Extrusion Spheronization—A Review," International Journal of PharnnTech Research. vol. 2, No. 4, pp. 2429-2433, Oct.-Dec. 2010 (Year: 2010).
Billington et al., "Effects of bile salts on the plasma membranes of isolated rat hepatocytes," Bichem. J. 188: 321-327, 1980.
Blackmore et al., "Polymorphisms in ABCB11 and ATP8B1 Associated with Development of Severe Intrahepatic Cholestasis in Hodgkin's Lymphoma," J Clin Exp Hepatol., 2013, 3(2):159-161.
Board of Appeal of European Patent Office, Case No. T 077/08-3.3.01, dated May 24, 2011, 17 pages.
Boncristani et al., Respiratory Viruses, Encyclopedia of Microbiology, 2009, 19 pages.
Bonge et al., "Cytostar-T Scintillating Microplate Assay for Measurement of Sodium-Dependent Bile Acid Uptake in Transfected HEK-293 Cells," Analytical Biochemistry, 2000, 282:94-101.
Bounford. University of Birmingham. Dissertation Abstracts International, (2016) vol. 75, No. IC. Order No. AA110588329. ProQuest Dissertations & Theses.
Bowel Diversion Surgeries: Ileostomy, Colostomy, Ileoanal Reservoir and Continent Ileostomy, US Department of Health and Human Services: National Institute of Diabetes and Digestive And Kidney Diseases, Feb. 2009, retrieved on Jan. 27, 2014, http://digestive.niddk.nih.gov/ddiseases/pub/ileostomy/Bowel_Diversion_508.pdf, 4 pages.
Brunt et al., "Nonalcoholic Steatohepatitis: A Proposal for Grading and Staging the Histological Lesions," American Jounral of Gastroenterology, Sep. 1999, 94(9): 2467-2474.
Brunzell and Hokanson, "Dislipidemia of Central Obesity and Insulin Resistance," Diabetes Care, 1999, 22(Suppl. 3):C10-C13.
Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.
Burrows, "Interventions for treating cholestasis in pregnancy," Cochrane Database Syst. Rev., 4:CD00493, 2001.
Byrn et al., "Pharmaceutical Solids: A Strategic Approach to Regulatory Considerations," Pharmaceutical Research, 1995, 12(7), pp. 945-954.
Byrne et al., "Missense mutations and single nucleotide polymorphisms in ABCB11 impair bile salt export pump processing and function or disrupt pre-messenger RNA splicing," Hepatology., 2009, 49(2):553-567.
Caira, "Crystalline Polymorphism of Organic Compounds," in: Topics in Current Chemistry, Jan. 1998, 198:163-208.
Camilleri, "Probiotics and irritable bowel syndrome: rationale, putative mechanisms, and evidence of clinical efficacy," Clin. Gastroenterol., 40(3):264-9, Mar. 2006.
Carulli et al., "Review article: effect of bile salt pool composition on hepatic and biliary functions," Aliment. Pharmacol. Ther. 2000, vol. 14, suppl. 2, p. 14-18.
Centeno, "Molecular mechanisms triggered by low-calcium diets," Nutrition research reviews., 22(2):163-74, Dec. 2009.
Chalasani et al., "The diagnosis and management of nonalcoholic fatty liver disease: Practice guidance from the American Association for the Study of Liver Diseases," Hepatology, 2018, 67(1):328-357.
Chang et al., "Bile acids promote the expression of hepatitis c virus in replicon-harboring cells," Journal of Virology, Sep. 2007, 81(18):9633-9640.
Chauhan et al., "Pharmaceutical polymers," Encycl. Biomed. Polymers and Polymeric Biomaterials, 2016, 5929-5942.
Chen et al., "Bile salt export pump is dysregulated with altered farnesoid X receptor isoform expression in patients with hepatocelular carcinoma," Hepatologu, 57: 4, 1530-1541, 2013.
Chen et al., "Diagnosis of BSEP/ABCB11 mutations in Asian patients with cholestasis using denaturing high performance liquid chromatography," J Pediatr., 2008, 153(6):825-832.
Chen et al., "FIC1 and BSEP defects in Taiwanese patients with chronic intrahepatic cholestasis with low gamma-glutamyltranspeptidase levels," Journal of Pediatrics, 2002, 140(1):119-124.
Chen et al., "Inhibition of apical sodium-dependent bile acid transporter as a novel treatment for diabetes," Am J Physiol Endocrinol Metab, 2012, 302:E68-E76.
Chen et al., "Progressive Familial Intrahepatic Cholestasis, Type 1, Is Associated with Decreased Farnesoid X Receptor Activity," Gastroenterology, 2004, 126:756-764.
Chen et al., "Serum and urine metabolite profiling reveals potential biomarkers of human hepatocellular carcinoma," Molecular and Cellular Proteomics 10.7, 2011.
Chen et al., "The effects of diets enriched in beta-glucans on blood lipoprotein concentrations," J. Clin. Lipidol., 3(3):154-8, May 2009.
Chen et al., "Treatment effect of rifampicin on cholestasis," Internet Journal of Pharmacology, 4(2), 2006.
Chey et al., "A Randomized Placebo-Controlled Phase II b Trial of A3309, A Bile Acid Transporter Inhibitor, for Chronic Idiopathic Constipation," Am. J. Gastroenterology, May 2011, 106:1803-1812.
Chiang, "Bile acids: regulation of synthesis," J. Lipid Res, 2009, 50(10):1955-1966.
Chourasia et al., "Polysaccharides for colon targeted drug delivery," Drug Delivery, Academic Press, vol. 11, No. 2, Jan. 1, 2004, 129-148, XP008060983.
Colorcon.com[online] "Achieving tablet stability with moisture management," retrived on May 28, 2021, retrieved from URL<https://www.colorcon.com/connect-with-colorcon/achieving-tablet-stability-with-moisture-management>, 4 pages.
Copeland et al., "Novel splice-site mutation in ATP8B1 results in atypical progressive familial intrahepatic cholestasis type 1," J Gastroenterol Hepatol., 2013, 28(3):560-564.
Danese et al., "Analytical evaluation of three enzymatic assays for measuring total bile acids in plasma using a fully-automated clinical chemistry platform," PLoS One, 2017, 12(6):e0179200.
Das & Kar., Non alcoholic steatohepatitis. JAPI. 53:, Mar. 2005.
Dashti et al., "A Phospholipidomic Analysis of All Defined Human Plasma Lipoproteins," Nature.com: Scientific Reports, Nov. 2011, DOI: 10.1038, 11 pages.
Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between

(56) References Cited

OTHER PUBLICATIONS

PFIC1 and PFIC2 and Natural History," Hepatology: Autoimmune, Cholestatic and Biliary Disease, May 2010, 1645-1655.
Davit-Spraul et al., "Liver transcript analysis reveals aberrant splicing due to silent and intronic variations in the ABCB11 gene," Mol Genet Metab., 2014, 113(3):225-229.
Dawson et al., "Bile acid transporters" J. Lipid Res. 2009, 50, 2340-2357.
Dawson, "Role of the intestinal bile acid transporters in bile acid and drug disposition," Handb. Exp. Pharmacol. 2011, 201:169-203.
De Lédinghen et al., "Controlled attenuation parameter for the diagnosis of steatosis in non-alcoholic fatty liver disease," J Gastroenterol Hepatol., 2016, 31(4):848-855.
Declaration in U.S. Appl. No. 15/137,323, dated Apr. 6, 2019, 7 pages.
Declaration in U.S. Appl. No. 16/699,478, dated Apr. 4, 2019, 21 pages.
DeFronzo et al., "Insuline resistance, A multisurfaced syndrome responsible for NIDDM, obesity, hypertension, dyslipidemia and atherosclerotic cardiovascular disease," Diabetes Care, 1991, 14:173-194.
Deng et al., "Novel ATP8B1 mutation in an adult male with progressive familial intrahepatic cholestasis," World J Gastroenterol., 2012, 18(44):6504-6509.
Di Lascio et al., "Steato-Score: Non-Invasive Quantitative Assessment of Liver Fat by Ultrasound Imaging," Ultrasound Med Biol., 2018, 44(8):1585-1596.
Di Padova et al., "Double-blind placebo-controlled clinical trial of microporous chlestyramine in the treatment of intra- and extra-hepatic cholestasis: relationship between itching and serum bile acids," Methods Find Exp Clin Pharmacol., Dec. 1984, 6(12):773-776 (Abstract Only).
DiBaise et al., "Bile Acids: An Underrecognized and Underappreciated Cause of Chronic Diarrhea", Pract. Gastroenterol. vol. 36(10), p. 32-44, 2012.
Dixon et al., "An expanded role for heterozygous mutations of ABCB4, ABCB11, ATP8B1, ABCC2 and TJP2 in intrahepatic cholestasis of pregnancy," Scientific Reports, 2017, 7(1):11823.
Dong et al., "Structure-activity relationship for FDA approved drugs as inhibitors of the human sodium taurocholate cotransporting polypeptide (NTCP).," Mol. Pharm. 2013, 10(3):1008-1019.
Dongiovanni et al., "Genetic Predisposition in NAFLD and NASH: Impact on Severity of Liver Disease and Response to Treatment," Curren Pharma Design, 2013, 19:5219-5238.
Dowling, "The enterohepatic circulation," Gastroenerology, 1972, 62(1):122-40.
Drage et al., "Exon-skipping and mRNA decay in human liver tissue: molecular consequences of pathogenic bile salt export pump mutations," Sci Rep., 2016, vol. 6: 24827.
Drage et al., "Sequencing of FIC1, BSEP and MDR3 in a large cohort of patients with cholestasis revealed a high number of different genetic variants," J Hepatol. 2017, 67(6):1253-1264.
Droge et al., Zeitschrift fur Gastroenterologie 2015, 53(12) Abstract No. A3-27. Meeting Info: 32. Jahrestagung der Deutschen Arbeitsgemeinschaft zum Studium der Leber. Dusseldorf, Germany. Jan. 22, 2016-Jan. 23, 2016.
Drumond et al., "Patients' appropriateness, acceptability, usability and preferences for pharmaceutical preparations: Results from a literature review on clinical evidence," Int. J. Pharm. 2017, 521(1-2):294-305.
EASL Clinical Practice Guidelines: Management of cholestatic liver diseases, European Assoc. for the Study of the Liver, Journal of Hepatology, 2009, 51:237-267.
Einspahr et al., "Protective role of wheat bran fiber: data from marker trials," Am. J. Med., 106(1A):32s-37s, Jan. 1999.
Eisai CO., Ltd., "Results from two phase 3 clinical trials of chronic constipation treatment" GOOFICE 5 mg tablet, The Lancet Gastro & Hepat., Jul. 9, 2018, 3 pages.
Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.
Ellinger et al., "Partial external biliary diversion in bile salt export pump deficiency: Association between outcome and mutation," World J Gastroenterol., 2017, 23(29):5295-5303.
Ellis et al., "Zebrafish abcb11b mutant reveals strategies to restore bile excretion impaired by bile salt export pump deficiency," Hepatology, 2018, 67(4)1531-1545.
Engelen et al., "Oral size perception of particles: effect of size, type, viscosity and method," J. Text. Studies 2005, 36(4):373-386.
Espenshade and Hughes, "Regulation of Sterol Synthesis in Eukaryotes," Annu. Rev. Genet., 2007, 41:401-427.
Evaluation of LUM001 in the Reduction of Pruritus in Alagille Syndrome (ITCH), Clinical Trials.gov, Feb. 5, 2014, retrieved on Oct. 3, 2014, http://clinicaltrials.gov/ct2/show/NCT02057692?term=LUM001&rank=5, 4 pages.
Evason et al., "Morphologic findings in progressive familial intrahepatic cholestasis 2 (PFIC2): correlation with genetic and immunohistochemical studies," Am J Surg Pathol., 2011, 35(5):687-696.
Evonik Industries, "Eudragit FS 30 D," Jul. 9, 2008, http://www.pharma-polymers.com.pharmapolymers/MCMbase/Pages/ProvideResource.aspx?respath=/NR/rdonlyres/BDD7E168-922E-4AB1-861F-EEEB58B85642/0/EUDRAGITFS30D_Promotiondatasheet_09072008.
Extended European Search Report in European Application No. 11840392.2, dated Feb. 24, 2014, 7 pages.
Extended European Search Report in European Application No. 11840481.3, dated Feb. 13, 2014, 10 pages.
Faubion et al., "Toxic bile salts induce rodent hepatocyte apoptosis via direct activation of Fas," The Journal of Clinical Investigation, 103: 1, 137-145, 1999.
Ferreira et al., Pediatric Transplantation 2013, 17(Suppl. 1):99. Abstract No. 239. Meeting Info: IPTA 7th Congress on Pediatric Transplantation. Warsaw, Poland. Jul. 13, 2013-Jul. 16, 2013.
Ferslew et al., "Altered Bile Acid Metabolome in Patients with Nonalcoholic Steatohepatitis," Dig Dis Sci., 2015, 60(11):3318-3328.
Fisher, "Milling of inactive pharmaceutical ingredients," Encyclopedia of Pharm. Tech., 2001, 2339-2351.
Folmer et al., "Differential effects of progressive familial intrahepatic cholestasis type 1 and benign recurrent intrahepatic cholestasis type 1 mutations on canalicular localization of ATP8B1," Hepatology., 2009, 50(5):1597-1605.
Forner et al., "Treatment of hepatocellular carcinoma," Critical Reviews in Oncology/Hematology, 2006, 60:89-98.
Francalanci et al., "Progressive familial intrahepatic cholestasis: Detection of new mutations and unusal modality of transmission," Digestive and Liver Disease 2010, 42(Suppl. 1):516, Abstract No. T.N.5.
Francalanci et al., Laboratory Investigation 2011, vol. 91, Supp. Suppl. 1, pp. 360A. Abstract No. 1526.
Fuentes-Zaragoza al., "Resistant Starch as functional ingredient: A review", , Food Research International, 43, 931-942, 2010.
Fuller, "Probiotics in man and animals," Appl. Bacterial. 1989, 66(5):365-378.
Gao et al., "Detection of hepatitis in children with idiopathic cholestatic bile salt export pump gene mutations," Shandong Yiyao, 2012, 52(10):14-16.
Gao et al., "Recent developments in the crystallization process: toward the pharmaceutical industry," Engineering, 2017, 3:343-353.
Gao et al., "The Identification of Two New ABCB11 Gene Mutations and the Treatment Outcome in a Young Adult with Benign Recurrent Intrahepatic Cholestasis: A Case Report," Hepatitis Monthly 2017, 17(10):e55087/1-e55087/6.
Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gibson and Roberfroid, "Dietary modulation of the human colonic microbiota: introducing the concept of prebiotics," J. Nutr. 1995, 125(6):1401-1412.

(56) References Cited

OTHER PUBLICATIONS

Gillberg et al., "The IBAT Inhibition by A3309—A Potential Mechanism for the Treatment of Constipation," Gastroenterology, 2010, 138(5), Supp 1, S-224.
Giovannoni et al., "Genetics and Molecular Modeling of New Mutations of Familial Intrahepatic Cholestasis in a Single Italian Center," PLoS One, 2015, 10(12):e0145021.
Glagov et al., "Compensatory enlargement of human athersclerotic coronary arteries," N Engl. J. Med., May 1987, 316(22):1371-1375 (Abstract Only).
Goldschmidt et al., "Increased frequency of double and triple heterozygous gene variants in children with intrahepatic cholestasis," Hepatol Res., 2016, 46(4):306-311.
Govers et al., "Characterization of the adsorption of conjugated and unconjugated bile acids to insoluble, amorphous calcium phosphate", Journal of Lipid Research 35(5):741-748, 1994.
Graffner et al., "The ileal bile acid transporter inhibitor A4250 decreases serum bile acids by interrupting the enterohepatic circulation," Alimentary Pharmacology and Therapeutics, 2015, 43(2):303-310.
Greten, "Molecular therapy for the treatment of hepatocellular carcinoma," Br. J. Cancer, 2009, 100:19-23.
Griffin, et al., "A novel gene mutation in ABCB11 in siblings with progressive familial intrahepatic cholestasis type 2," Canadian Journal of Gastroenterology and Hepatology 2016, vol. 2016. Abstract No. A200. Meeting Info: 2016 Canadian Digestive Diseases Week, CDDW 2016. Montreal, QC, United States. Feb. 26, 2016-Feb. 29, 2016.
Gunaydin et al., "Progressive familial intrahepatic cholestasis: diagnosis, management, and treatment," Hepat Med., 2018, 10:95-104.
Guorui et al., "Genetic diagnosis of progressive familial intrahepatic cholestasis type 2," Linchuang Erke Zazhi, 2013, 31(10):905-909.
Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.
Hancock et al., "Molecular Mobility of amorphous pharmaceutical solids below their glass transition temperatures," 12(6): 799-806, 1995.
Hao et al., "Application of high-throughput sequencing technologies with target capture/target next-generation sequencing in diagnosis of neonatal intrahepatic cholestasis causes by citrin deficiency (NICDD)," International Journal of Clinical and Experimental Pathology, 2017, 10(3):3480-3487.
Harmanci et al., "Late onset drug induced cholestasis in a living-related liver transplantation donor to son with progressive familial intrahepatic cholestasis," Experimental and Clinical Transplantation 2015, 13(2):76, Abstract No. P62. Meeting Info: 1st Congress of the Turkic World Transplantation Society. Astana, Kazakhstan. May 20, 2015-May 22, 2015.
Hasegawa et al., "Intractable itch relieved by 4-phenylbutyrate therapy in patients with progressive familial intrahepatic cholestasis type 1," Orphanet J Rare Dis., 2014, 9:89.
Hayashi et al., "Assessment of ATP8B1 Deficiency in Pediatric Patients With Cholestasis Using Peripheral Blood Monocyte-Derived Macrophages," EBioMedicine, 2018, 27:187-199.
Hayashi et al., "Successful treatment with 4-phenylbutyrate in a patient with benign recurrent intrahepatic cholestasis type 2 refractory to biliary drainage and bilirubin absorption," Hepatol Res., 2016, 46(2):192-200.
Heathcote, "Management of primary biliary cirrhosis," Hepatology, 2000, 31(4):1005-1013.
hepc.liverfoundation.org [online]. "Nonalcoholic Fatty Liver Disease," Brochure, 2016 [retrieved on Feb. 1, 2018]. Retrived from the Internet: URL<http://hepc.liverfoundation.org/wp-content/uploads/2012/07/NAFLD-Brochure-2016.pdf>, 8 pages.
Herbst et al., "Taking the next step forward—Diagnosing inherited infantile cholestatic disorders with next generation sequencing," Mol Cell Probes, 2015, 29(5):291-298.
Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.
Ho et al., "Polymorphic variants in the human bile salt export pump (BSEP; ABCB11): functional characterization and interindividual variability," Pharmacogenet Genomics, 2010, 20(1):45-57.
Hoffman et al., Human Anatomy, picture of the colon, p. 1-7, https://www.webmd.com/digestive-disorders/picture-of-the-colon #1, Accesses Aug. 4, 2019.
Hollands et al., "Ileal exclusion for Byler's disease: an alternative surgical approach with promising early results for pruritus," Journal of Pediatric Surgery, Feb. 1988, 33(2): 220-224.
Holz et al., "Can genetic testing guide the therapy of cholestatic pruritus? A case of benign recurrent intrahepatic cholestasis type 2 with severe nasobiliary drainage-refractory itch," Hepatol Commun., 2018, 2(2):152-154.
Holz et al., "Plasma separation and anion adsorption results in rapid improvement of nasobiliary drainage (NBD)-refractory pruritus in BRIC type 2," Zeitschrift fur Gastroenterologie 2016, vol. 54, No. 8. Abstract No. KV275. Meeting Info: Viszeralmedizin 2016, 71. Jahrestagung der Deutschen Gesellschaft fur Gastroenterologie, Verdauungs- und Stoffwechselkrankheiten mit Sektion Endoskopie—10. Herbsttagung derDeutschen Gesellschaft fur Allgemein- und Viszeralchirurgie. Hamburg, Germany. Sep. 21, 2016-Sep. 24, 2016.
Hsu et al., "Adult progressive intrahepatic cholestasis associated with genetic variations in ATP8B1 and ABCB11," Hepatol Res., 2009, 39(6):625-631.
Hu et al., "Diagnosis of ABCB11 gene mutations in children with intrahepatic cholestasis using high resolution melting analysis and direct sequencing," Mol Med Rep., 2014, 10(3):1264-1274.
Huang et al., "Discovery of Potent, Nonsystemic Apical Sodium-Codependent Bile Acid Transporter Inhibitors (Part 2)," J. Med. Chem., 2005, 48:5853-5868.
IBAT inhibitor A4250 for Cholestatic Pruritus, ClinicalTrials.gov, Last updated Feb. 10, 2015, https://clinicaltrials.gov/ct2/show/NCT02360852?term=a4250&rank=1, 3 pages.
Imagawa et al., "Clinical phenotype and molecular analysis of a homozygous ABCB11 mutation responsible for progressive infantile cholestasis," J Hum Genet. 2018, 63(5):569-577.
Imagawa et al., "Generation of a bile salt export pump deficiency model using patient-specific induced pluripotent stem cell-derived hepatocyte-like cells," Sci Rep., 2017, 7:41806.
Imagawa et al., "Splicing analysis using induced pluripotent stem cell-derived hepatocyte-like cells generated from a patient with progressive familial intrahepatic cholestatsis type 2," Journal of Pediatric Gastroenterology and Nutrition 2016, 63(2):551, Abstract No. 166, Meeting Info: World Congress of Pediatric Gastroenterology, Hepatology and Nutrition 2016. Montreal, QC, Canada. Oct. 5, 2016-Oct. 8, 2016.
Initiation of a Phase II Trial for A4250, the Company's Lead Compound for Cholestatic Liver Diseases and NASH, Albireo Pharma Press Release, Feb. 5, 2015, http://www.alberiopharma.com/News.aspx?PageID=1600872, 2 pages.
International Preliminary Report on Patentability for Application No. PCT/JP2015/068240, dated Jan. 5, 2017, 12 pages (with English translation).
International Preliminary Report on Patentability for International Application No. PCT/EP2015/074573, dated Apr. 25, 2017, 8 pages.
International Preliminary Report on Patentability for International Application No. PCT/SE2011/051335, dated May 23, 2011, 7 pages.
International Preliminary Report on Patentability for International Application No. PCT/SE2011/051336, dated May 23, 2013, 11 pages.
International Search Report and Written Opinion for Application No. PCT/EP2014/058432, dated Jul. 11, 2014, 9 pages.
International Search Report and Written Opinion for Application No. PCT/SE2017/050126, dated Apr. 24, 2017, 27 pages.
International Search Report and Written Opinion for Application No. PCT/SE2017/050127, dated May 8, 2017, 16 pages.
International Search Report and Written Opinion for Application No. PCT/SE2017/050128, dated May 8, 2017, 16 pages.

(56) References Cited

OTHER PUBLICATIONS

International Search Report and Written Opinion for Appln. No. PCT/EP2019/064602, dated Aug. 9, 2019, 11 pages.
International Search Report and Written Opinion for International Application No. PCT/EP2015/074573, dated Apr. 28, 2016, 11 pages.
International Search Report and Written Opinion for International Application No. PCT/SE2011/051335, dated Feb. 3, 2012, 12 pages.
International Search Report and Written Opinion for International Application No. PCT/SE2011/051366, dated Feb. 22, 2012, 18 pages.
International Search Report and Written Opinion in Appln. No. PCT/SE2019/050603, dated Sep. 18, 2019, 11 pages.
International Search Report and Written Opinion in International Application No. PCT/SE2018/050802, dated Oct. 26, 2018, 14 pages.
International Search Report and Written Opinion in International Application No. PCT/SE2018/050803, dated Oct. 26, 2018, 14 pages.
International Search Report and Written Opinion in International Appln. No. PCT/EP2020/052940, dated Mar. 23, 2020, 12 pages.
International Search Report and Written Opinion in International Appln. No. PCT/EP2020/052942, dated Mar. 23, 2020, 9 pages.
International Search Report, Application No. PCT/JP2015/068240, dated Sep. 15, 2015, 11 pages (with English translation).
Ishak et al., "Histological grading and staging of chronic hepatitis," J. Hepatol. 1995, vol. 22, p. 696-699.
Ishibashi et al., "Hypercholesterolemia in low density lipoprotein receptor knockout mice and its reversal by adenovirus-mediated gene delivery", Journal of Clinical Investigation 92(2):883-893, 1993.
Islam and Di Baise, "Bile Acids: An underrecognized and under-appreciated cause of chronic diarrhea," Pract. Gastroenterol. 2012, vol. 36(10), p. 32-44.
Ivashkin et al., "A novel mutation of ATP8B1 gene in young patient with familial intrahepatic cholestasis.," Hepatology International 2016, 10(1):5461, Abstract No. LBO-38. Meeting Info: 25th Annual Conference of the Asian Pacific Association for the Study of the Liver, APASL 2016. Tokyo, Japan. Feb. 20, 2016-Feb. 24, 2016.
Jacobsen et al., "Effect of enterocoated cholestyramine on bowel habit after ileal resection: a double blind crossover study," Br. Med. J. 1985, vol. 290, p. 1315-1318.
Jacquet et al., "Alagille Syndrome in Adult Patients: It is Never Too Late," American Journal of Kidney Diseases, May 2007, 49(5):705-709.
Jankowska et al., "[Cholestatic liver disease in children]," Przegl. Epidemiol., 56:16-21, 2002.
Jankowska et al., "Ileal exclusion in children with progressive familial intrahepatic cholestasis," J Pediatr Gastroenterol Nutr. 2014,58(1):92-95.
Jansen et al., "Endogenous bile acids as carcinogens," Journal of Hepatology, Sep. 2007, 47(3):434-435.
Jaquotot-Haerranz et al., "Clinical variability of mutations in the ABCB11 gene: a case report," Rev Esp Enferm Dig., 2013, 105(1):52-54.
Jericho et al., "Bile Acid Pool Dynamics in Progressive Familial Intrahepatic Cholestasis with Partial External Bile Diversion," Journal of Pediatric Gastroenterology and Nutrition, 2015, 60(3):368-374.
Jiang et al., "Non alcoholic steatohepatitis a precursor for hepatocellular carcinoma development," World Journal of Gastroenterology: WJG, Nov. 28, 2014, 20(44):16464-16473.
Jirsa et al., "Indel in the FIC1/ATP8B1 gene—a novel rare type of mutation associated with benign recurrent intrahepatic cholestasis," Hepatol Res. 2004, 30(1):1-3.
Jung et al., "Prenatal molecular diagnosis of inherited cholestatic diseases," J Pediatr Gastroenterol Nutr. 2007, 44(4):453-458.

Kagawa et al., "Phenotypic differences in PFIC2 and BRIC2 correlate with protein stability of mutant Bsep and impaired taurocholate secretion in MDCK II cells," Am J Physiol Gastrointest Liver Physiol., 2008, 294(1):G58-67.
Kang et al., "Progressive Familial Intrahepatic Cholestasis in Korea: A Clinicopathological Study of Five Patients," J Pathol Transl Med. May 16, 2019, 53(4):253-260.
Karpen and Dawson, "Not all (bile acids) who wander are lost: the first report of a patient with an isolated NTCP defect," Hepatology, 2015, 61(1):24-27.
Khosla et al., "Recurrent Post-partum Jaundice: Rare Genetic Disorder With Novel Genetic Mutations Identified," American Journal of Gastroenterology 2015, 110(1):S397. Meeting Info.: 80th Annual Scientific Meeting of the American-College-of-Gastroenterology. Honolulu, HI, USA. Oct. 16-21, 2015.
Kim, "Novel mutation of ABCB11 heterozygote associated with transient neonatal intrahepatic cholestasis," Journal of Pediatric Gastroenterology and Nutrition 2016, 62(1):620, Abstract No. H-P-045. Meeting Info: 49th Annual Meeting of the European Society for Pediatric Gastroenterology, Hepatology and Nutrition, ESPGHAN 2016. Athens, Greece. May 25, 2016-May 28, 2016.
Kleiner et al., "Design and validation of a histological scoring system for nonalcoholic fatty liver disease," Hepatology, 2005, 41(6):1313-1321.
Klomp et al., "Characterization of mutations in ATP8B1 associated with hereditary cholestasis," Hepatology, 2004, 40(1):27-38.
Knisely et al., "Hepatocellular Carcinoma in ten children under five years of age with bile salt export pump deficiency," Hepatology, Aug. 2006, 44(2):478-486.
Kolter et al., "Structure and dry binding activity of different polymers, including Kollidon VA 64," Drug Development, 2000, 26(11):1159-65.
Kooistra, et al., "KLIFS: A structural kinase-ligand interaction database," Nucleic Acids Res., 2016, vol. 44, No. D1, pp. D365-D371.
Korman et al., "Assessment of Activity in Chronic Active Liver Disease," New England Journal of Medicine, 2010, 290(25):1399-1402.
Kosters et al., "Bile acid transporters in health and disease," Xenobiotica 2008, 38(7-8):1043-1071.
Kozarewicz, "Regulatory perspectives on acceptability testing of dosage forms in children," Int. J. Pharm. 2014, 469(2):245-248.
Krawczyk et al., "Prolonged cholestasis triggered by hepatitis A virus infection and variants of the hepatocanalicular phospholipid and bile salt transporters," Ann Hepatol., 2012, 11(5):710-744.
Kumar and Tandon, "Use of ursodeoxycholic acid in liver diseases," J. Gastroenterology and Hepatology, 2001, 16:3-14.
Kumar et al., "Cholestatic presentation of chronic hepatitis c." Dig. Dis. Sci, 2001, 46(10):2066-2073.
Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.
Kurbegov et al., Biliary diversion for progressive familial intrahepatic cholestasis: Improved liver morphology and bile acid profile, Gastroenterology, 125: 4, 1227-1234, 2003.
Lam et al., "A patient with novel ABCB11 gene mutations with phenotypic transition between BRIC2 and PFIC2," J Hepatol. 2006, 44(1):240-242.
Lam et al., "Levels of plasma membrane expression in progressive and benign mutations of the bile salt export pump (Bsep/Abcb11) correlate with severity of cholestatic diseases," Am J Physiol Cell Physiol. 2007, 293(5):C1709-16.
Lang et al.,. "Genetic variability, haplotype structures, and ethnic diversity of hepatic transporters MDR3 (ABCB4) and bile salt export pump (ABCB11)," Drug Metab Dispos. 2006, 34(9):1582-1599.
Lang et al., "Mutations and polymorphisms in the bile salt export pump and the multidrug resistance protein 3 associated with drug-induced liver injury," Pharmacogenet Genomics, 2007, 17(1):47-60.
Lanzini et al., "Intestinal absorption of the bile acid analogue $^{75}$Se-homocholic acid-taurine is increased in primary biliary cirrho-

(56) References Cited

OTHER PUBLICATIONS sis and reverts to normal during ursodeoycholic acid administrations," Gut, 2003, 52:1371-1375.
Lee et al., "Early Diagnosis of ABCB11 Spectrum Liver Disorders by Next Generation Sequencing," Pediatr Gastroenterol Hepatol Nutr. 2017, 20(2):114-123.
Lewis et al., "Effects of 2164U90 on ileal bile acid adsorption and serum cholesterol in rats and mice", Journal of Lipid Research 36(5):1098-1105, 1995.
Li et al., "ATP8B1 and ABCB11 mutations in Chinese patients with normal gamma-glutamyl transferase cholestasis: Phenotypic differences between progressive familial intrahepatic cholestasis type 1 and 2," Hepatology International 2017, 11(1):S180. Abstract No. OP284.
Li et al., "Clinical feature and gene mutation analysis of one pedigree with progressive familial intrahepatic cholestasis type II," Hepatology International 2017, 11(1):S362, Abstract No. PP0347. Meeting Info: 26th Annual Conference of the Asian Pacific Association for the Study of the Liver, APASL 2017. Shanghai, China. Feb. 15, 2017-Feb. 19, 2017.
Li et al., "Effect of Resistant Starch Film Properties on the Colon-Targeting Release of Drug From Coated Pellets", 152 J Control. Rel. e5, 2011.
Lichtinghagen R, et al., "The Enhanced Liver Fibrosis (ELF) score: normal values, influence factors and proposed cut-off values," J Hepatol. Aug. 2013;59(2):236-42.
Lin et al., "[Clinical and genetic analysis of an infant with progressive familial intrahepatic cholestasis type II].," Zhongguo Dang Dai Er Ke Za Zhi. 2018, 20(9)758-764 (with English abstract).
Ling, "Congenital cholestatic syndromes: What happens when children grow up?," Can J Gastroenterol, Nov. 11, 2007, 21(11):743-751.
Liu et al., "ABCB11 gene mutations in Chinese children with progressive intrahepatic cholestasis and low gamma glutamyltransferase," Liver International 2010, 30(6):809-815.
Liu et al., "Association of variants of ABCB11 with transient neonatal cholestasis," Pediatr Int. 2013, 55(2):138-144.
Liu et al., "Characterization of ATP8B1 gene mutations and a hot-linked mutation found in Chinese children with progressive intrahepatic cholestasis and low GGT," J Pediatr Gastroenterol Nutr., 2010, 50(2):179-183.
Liu et al., "Characterization of ATP8B1 mutations and a hot linked mutation found in Chinese children with progressive intrahepatic cholestasis and low GGT," Hepatology International 2009, 3(1):184-185, Abstract No. PE405. Meeting Info: 19th Conference of the Asian Pacific Association for the Study of the Liver. Hong Kong, China. Feb. 13, 2009-Feb. 16, 2009.
Liu et al., "Homozygous p.Ser267Phe in SLC10A1 is associated with a new type of hypercholanemia and implications for personalized medicine," Scientific Reports, 2017, 7(9214):1-7.
Liu, et al., "Patient-centered pharmaceutical design to improve acceptability of medicines: similarities and differences in paediatric and geriatric populations," Drugs 2014, 74(16):1871-1889.
Loh et al., "Overview of milling techniques for improving the solubility of poorly water-soluble drugs," Asian J Pharm Sci., 2015, 10:225-274.
Longo et al., "Hyperlipidemia in chronic cholestatic liver disease," Curr. Treat. Options Gastrenterol., 2001, 4:111-114.
Lopez et al., "Effect of formulation variables on oral grittiness and preferences of multiparticulate formulations in adult volunteers," Eur. J. Pharm. Sci. 2016, 92:156-162.
Lopez et al., "Formulation approaches to pediatric oral drug delivery: benefits and limitations of current platforms," Expert Opin. Drug Deliv., 2015, 12(11):1727-1740.
Lumena Pharmaceuticals Now Dosing Patients in the INDIGO Phase 2 Clinical Trial of LUM001 in Pediatric Patients with Progressive Familial Intrahepatic Cholestasis, PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.
Lv et al., "Noninvasive Quantitative Detection Methods of Liver Fat Content in Nonalcoholic Fatty Liver Disease," J Clin Transl Hepatol. 2018, 6(2):217-221.
Lykavieris et al., "Outcome of liver disease in children with Alagille syndrome: a study of 163 patients," Gut, 2001, 49:431-435.
Maggiore et al., "Relapsing features of bile salt export pump deficiency after liver transplantation in two patients with progressive familial intrahepatic cholestasis type 2," J Hepatol. 2010, 53(5):981-6.
Manghat and Wierzbicki, "Colesevelam hydrochloride: a specifically engineered bile acid sequestrant," Future Lipidology, 3(3):237-255, Jun. 2008.
Marzorati et al., "A novel hypromellose capsule, with acid resistance properties, permits the targeted delivery of acid-sensitive products to the intestine," LWT-Food Sci. Techno.1 2015, vol. 60, p. 544-551.
Masahata et al., "Recurrence of Progressive Familial Intrahepatic Cholestasis Type 2 Phenotype After Living-donor Liver Transplantation: A Case Report," Transplant Proc. 2016, 48(9):3156-3162.
Massei et al., "Cholestasis as a presenting feature of acute epstein-barr virus infection," The pediatric Infectious Disease J., Feb. 2001, 5 pages.
Matte et al., "Analysis of gene mutations in children with cholestasis of undefined etiology," J Pediatr Gastroenterol Nutr. 2010, 51(4):488-493.
McCullough et al., "The epidemiology and risk factors of NASH.", Blackwell Publishing, Chapter 3, 2005.
McKay et al., "Mutation detection in cholestatic patients using microarray resequncing of ATP8B1 and ABCB11 [version 2; peer review: 2 approved, 1 approved with reservations]," F1000 Res., 2013, 2:32.
McMichael and Potter, "Reproduction, endogenous and exogenous sex hormones, and colon cancer: a review and hypothesis," J. Natl. Cancer Inst., 65(6):1201-07, Dec. 1980.
McPherson et al., "Simple non-invasive fibrosis scoring systems can reliably exclude advanced fibrosis in patients with non-alcoholic fatty liver disease," Gut 2010, 59(9):1265-9.
MerckManuals.com, "Obesity," 2008, Merch Manual for Health Care Professionals, Section—Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Michielsen et al., "Viral hepatitis and hepatocellular carcinoma," World Journal of Surg. Oncol, May 2005, 3(27):1-18.
Miloh et al., Gastroenterology, Meeting Info.: Digestive Disease Week Meeting/107th Annual Meeting of the American-GastroenterologicalAssociation. Los Angeles, CA, USA. May 2006, 130:(4)(2): A759-A760.
Minekus et al., "A computer-controlled system to simulate conditions of the large intestine with peristaltic mixing, water absorption and absorption of fermentation products," Appl. Microbiol Biatechnol. 1999, 53(1):108-114.
Mirum Corporate Presentation,Presentation, Aug. 2019, 38 slides.
Mishra et al., "Investigation of organoleptic characteristics in the development of soft chews of calcium carbonate as mineral supplement," Yakugaku Zasshi 2009, 129(12):1537-1544.
Mistry et al., "Evidence of acceptability of oral paediatric medicines: a review," J. Pharm. Pharmacol. 2017, 69(4):361-376.
Mizuochi et al., "Characterization of urinary bile acids in a pediatric BRIC-1 patient: effect of rifampicin treatment," Clin Chim Acta. 2012, 413(15-16):1301-1304.
Moghadamrad et al., "Cholestasis in a patient with gallstones and a normal gamma-glutamyl transferase," Hepatology, 2013, 57(6):2539-2541.
Molly et al., "Development of a 5-step multi-chamber reactor as a simulation of the human intestinal microbial system," Appl. Microbiol. Biatechnol. 1993, 39:254-258.
Morissette et al., "High-throughput crystallization: polymorphs, salts, co-crystals and solvates of pharmaceutical solids," Advanced Drug Delivery Reviews, 2004, 56:275-300.

(56) References Cited

OTHER PUBLICATIONS

Morotti et al., "Progressive Familial Intrahepatic Cholestasis (PFIC) Type 1, 2, and 3: A Review of the Liver Pathology Findings," Seminars in Liver Disease, Feb. 2011, 31(1):3-10.

Mouzaki and Allard, "Non-alcoholic steatohepatitis: the therapeutic challenge of a global epidemic," Annals of Gastroenterology, 2012, 25: 207-217.

Mowat et al., "Respiratory chain complex III [correction of complex] in deficiency with pruritus: a novel vitamin responsive clinical feature," J. Pediatr., 134(3):352-4, Mar. 1999.

Mwesigwa et al., "An investigation into moisture barrier fil coating efficacy and its revelance to drug stability in solid dosage forms," Int. J. of Pharmacies, Jan. 2016, 497:70-77.

Nagasaka et al., "Depletion of high-density lipoprotein and appearance of triglyceride-rich low-density lipoprotein in a Japanese patient with FIC1 deficiency manifesting benign recurrent intrahepatic cholestasis," J Pediatr Gastroenterol Nutr., 2007, 45(1)96-105.

Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.

Narchi et al., "Intrahepatic cholestasis in two omani siblings associated with a novel homozygous ATP8B1 mutation, c.379C>G (p.L127V).," Saudi J Gastroenterol. 2017, 23(5):303-305.

Neuman, et al., "Biomarkers in nonalcoholic fatty liver disease," Can. J. Gastroenterol. Hepatol. 2014, 28(11):607-618.

Neuvonen et al., "Activated charcoal in the treatment of hypercholesterolaemia: dose-response relationships and comparison with cholestyramine," Eur J Clin Pharnnacol, 1989, 37(3):225.

Ng et al., "Autoimmune haemolytic anaemia with giant cell hepatitis and concurrent bile salt export pump deficiency: Challenges in diagnosis and management," Journal of Pediatric Gastroenterology and Nutrition 2018, 66(2):860, Abstract No. H-P-127. Meeting Info: 51st Annual Meeting European Society for Paediatric Gastroenterology, Hepatology and Nutrition, ESPGHAN 2018. Geneva, Switzerland. May 9, 2018-May 12, 2018.

Noe et al., "Impaired expression and function of the bile salt export pump due to three novel ABCB11 mutations in intrahepatic cholestasis," J Hepatol. 2005, 43(3):536-543.

O'Neill et al.,"Comparison of efficacy of plant stanol ester and sterol ester: short-term and longer-term studies," American Journal of Cardiology, 96(1A):29d-36D, Jul. 2005.

Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan. 10, 2013), 102(1), pp. 83-89.

Open Label Study to Evaluate Efficacy and Long Term Safety of LUM001 in the Treatment of Cholestatic Liver Disease in Patients With Progressive Familial Intrahepatic Cholestasis (INDIGO), Clinical Trials.gov, Feb. 5, 2014, retrieved on Oct. 3, 2014, http://clinicaltrials.gov/ct2/show/NCT02057718?term=LUM001&rank=4, 3 pages.

Open Label Study to Evaluate Safety and Efficacy of LUM001 in Patients With Primary Sclerosing Cholangitis (CAMEO), Clinical Trials.gov, Feb. 11, 2014, retrieved Oct. 3, 2014, http://clinicaltrials.gov/ct2/show/NCT02061540?term=LUM001&rank=6, 3 pages.

Pai et al. Compression and evaluation of extended release matrix pellets prepared by the extrusion/spheronization process into disintegrating tablets. Brazilian Journal of Pharmaceutical Sciences. vol. 48, n. 1, janinnar., 2012 (Year: 2012).

Painter et al., "Sequence variation in the ATP8B1 gene and intrahepatic cholestasis of pregnancy," Eur J Hum Genet. 2005, 13(4):435-439.

Park et al., "Clinical and ABCB11 profiles in Korean infants with progressive familial intrahepatic cholestasis," World J Gastroenterol., 2016, 22(20):4901-4907.

Parker et al., "Molecular mechanisms underlying bile acid-stimulated glucagon-like peptide-1 secretion," British J. Pharmacology, 2012, 165:414-423.

Patani et al., "Bioisosterism: A Rational Approach in Drug Design," Chem Rev, 1996, 96:3147-3176.

Pattni and Walters, "Recent advances in the understanding of bile acid malabsorption," Br. Med. Bull. 2009, vol. 92, p. 79-93.

Pauli-Magnus et al., "Enterohepatic transport of bile salts and genetics of cholestasis," Journal of Hepatology, 2005, 43(2):342-357.

Pauli-Magnus et al., "Impaired expression and function of the bile salt export pump due to three novel ABCB11 mutations in intrahepatic cholestasis," Hepatology 2003, vol. 38, No. 4 Suppl. 1, pp. 518A. print. Meeting Info.: 54th Annual Meeting of the American Association for the Study of Liver Diseases. Boston, MA, USA. Oct. 24-28, 2003. American Association for the Study of Liver Diseases.

PCT International Search Report and Written Opinion in Application No. PCT/SE2019/050208, dated Jul. 8, 2019, 15 pages.

PCT International Search Report and Written Opinion in International Appln No. PCT/EP2020/084569, dated Mar. 9, 2021, 13 pages.

PCT International Search Report and Written Opinion in International Appln. No. PCT/EP2020/084567, dated Feb. 11, 2021, 13 pages.

PCT International Search Report and Written Opinion in International Appln. No. PCT/EP2020/084568, dated Feb. 11, 2021, 13 pages.

PCT International Search Report and Written Opinion in International Appln. No. PCT/EP2020/084570, dated Feb. 11, 2021, 13 pages.

PCT International Search Report and Written Opinion in International Appln. No. PCT/EP2020/084571, dated Feb. 4, 2021, 14 pages.

Peng et al., "[Relationship between phenotype and genotype of ABCB11 deficiency in siblings and literature review].," Zhonghua er ke za zhi (Chinese journal of pediatrics) 2018, 56(6):440-444.

Perez et al., "Bile-acid-induced cell injury and protection," World J Gastroenterol, Apr. 2009, 15(14)1677-1689.

Perumpail et al., "Clinical epidemiology and disease burden of nonalcoholic fatty liver disease," World Journal of Gastroenterology, Dec. 2017, 23(47): 8263-8276.

Phase 2 Study to Evaluate LUM001 in Combination With Ursodeoxycholic Acid in Patients With Primary Biliary Cirrhosis (CLARITY), Clinical Trials.gov, Jul. 17, 2013, retrieved Oct. 3, 2014, http://clinicaltrials.gov/ct2/show/NCT01904058?term=LUM001&rank=8, 3 pages.

Plump et al., "Severe hypercholesterolemia and atherosclerosis in apolipoprotein E-deficient mice created by homologous recombination in ES cells", Cell (71):343-353, 1992.

Podesta et al., "Treatment of pruritus of primary biliary cirrhosis with rifampin," Dig. Dis. Sci, 1991, 36(2):216-220.

Possemiers et al., "PCR-DGGE-based quantification of stability of the microbial community in a simulator of the human intestinal microbial ecosystem," FEMS Microbiol. Ecol. 2004, vol. 49, p. 495-507.

Poupon et al., "Chronic Cholestatic Disease," J. Hepatology, 2000, 32(1):12-140.

Progressive familial intrahepatic cholestasis, Wikipedia, the free encyclopedia, posted on or about Feb. 24, 2006, http://en.wikipedia.org/wiki/Progressive_familial_intrahepatic_cholestasis, 3 pages.

Qiu et al., "Defects in myosin VB are associated with a spectrum of previously undiagnosed low γ-glutamyltransferase cholestasis," Hepatology 2017, 65(5)1655-1669.

Qiu et al., "Disruption of BSEP function in HepaRG cells alters bile acid disposition and is a susceptive factor to drug-induced cholestatic injury," Mol. Pharmaceutics, 13:4,, 2016 (Abstract only).

Rancaniello, "How many viruses on earth?" Virology Blog, Sep. 2013, 6 pages.

Reeder et al., "Quantitative assessment of liver fat with magnetic resonance imaging and spectroscopy," J Magn Reson Imaging. 2011, 34(4):729-749.

Renga et al., "Role of FXR in regulating bile acid homeostasis and relevance for human diseases," Curr. Drug. Targets Immune Endocr. Metabol. Disord., 5(3):289-303, Sep. 2005.

Report EC20082069.02.01 dated Feb. 2009, filed with appellant's letter of Apr. 26, 2011.

(56) References Cited

OTHER PUBLICATIONS

Report filed at oral proceedings before opposition division, GMS-CFEP-2007-20, "Filtration and Drying Study on Amorphous and Form IV Atorvastatin Calcium," 2007.
Ricci, "Bridging studies in support of oral pediatric formulation development," Int. J. Pharmaceuticals, 2013, 457:323-326.
Rolo et al., "Bile acids affect liver mitochondrial bioenergetics: Possible relevance for cholestasis therapy," Toxocological Sciences, 57: 177-185, 2000.
RU Office Action in Russian Appln. No. 2018131255, dated May 19, 2020, 16 pages (with English translation).
Rumbo et al., Transplantation 2018, vol. 102, No. 7, Supp. Supplement 1, pp. 5848. Abstract No. P.752. Meeting Info: 27th International Congress of The Transplantation Society, TTS 2018. Madrid, Spain. Jun. 30, 2018-Jul. 5, 2018.
Ryder, "Guidelines for the diagnosis and treatment of hepatocellular carcinoma (HCC) in adults," Gut, May 2003, 52:(Suppl.111):iii1-iii8.
Safety and Efficacy Study of LUM001 in the Treatment of Cholestatic Liver Disease in Patients With Alagille Syndrome (IMAGO), Clinical Trials.gov, Jul. 16, 2013, http://clinicaltrials.gov/ct2/show/NCT01903460?term=LUM001&rank=1, 3 pages.
Sanyal et al. The etiology of hepatocellular carcinonna and consequences of treatment. The Oncologist, 2010, 15 Suppl 4, 14-22.
Satapathy and Sanyal, "Epidemiology and Natural History of Non-alcoholic Fatty Liver Disease," Seminars in Liver Disease, Aug. 2015, 35(3): 221-235.
Sattler et al., "Functional analysis of previously uncharacterised disease-causing mutations of the bile salt export pump," Journal of Hepatology 2017, 66(1):5177. Meeting Info.: International Liver Congress/ 52nd Annual Meeting of the European-Association-for-the-Studyof- the-Liver. Amsterdam, Netherlands. Apr. 19-23, 2017. European Assoc Study Liver.
Scheimann et al., "Prevalence of Abcb 11 mutations among children with cholelithiasis," Gastroenterology 2007, 132(4)Suppl. 2:A452, Meeting Info.: Digestive Disease Week Meeting/108th Annual Meeting of the American-GastroenterologicalAssociation. Washington, DC, USA. May 19-24, 2007. Amer Gastroenterol Assoc; Amer Assoc Study Liver Dis; Amer Soc Gastrointestinal Endoscopy; Soc Surg Alimentary Tract.
Scheuer, "Primary Biliary Cirrhosis," Proc. R. Soc. Med., Dec. 1967, 60:1257-1260.
Schiller, "Review article: the therapy of constipation", Alimentary Pharmacology and Therapeutics 15(6):749-763, 2001.
Schumpelick et al., "[Ulcerative colitis—late functional results of ileoanal pouch anastomosis]," Chirung, 69(10):1013-19, Oct. 1998.
Sciveres. "Relapsing features of bile salt export pump (BSEP) deficiency in a patient successfully transplanted for progressive familial intrahepatic cholestasis type 2 (PFIC2).," Digestive and Liver Disease 2010, 42(5):5329. Abstract No. CO18. Meeting Info: 17th National Congress SIGENP. Pescara, Italy. Oct. 7, 2010-Oct. 9, 2010.
Shah et al., "Progressive Familial Intrahepatic Cholestasis Type 2 in an Indian Child," J Pediatr Genet. 2017, 6(2):126-127.
Shah et al., "Role of Caco-2 Cell Monolayers in Prediction of Intestinal Drug Absorption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastrointest Liver Physiol, 2010, 298:G419-G424.
Shaprio et al., "DHPLC screening for mutations in progressive familial intrahepatic cholestasis patients," J Hum Genet. 2010, 55(5):308-313.
Sharma et al., "Spectrum of genomic variations in Indian patients with progressive familial intrahepatic cholestasis," BMC Gastroenterol, 2018, 18(1):107.
Sharma et al., "Spectrum of sequence variations in Indian patients with progressive familial intrahepatic cholestasis show several novel polymorphisms," Indian Journal of Gastroenterology 2017, 36(1):A99. Abstract No. M-20. Meeting Info: 58th Annual Conference of the Indian Society of Gastroenterology, ISGCON 2017. Bhubaneswar, India. Dec. 14, 2017-Dec. 17, 2017.
Sherrif et al., "Hepatotoxicity from anabolic androgenic steroids marketed as dietary supplements: contribution from ATP8B1/ABCB11 mutations?," Liver international: official journal of the International Association for the Study of the Liver, 2013, 33(8):1266-1270.
Shimizu et al., "Living-related liver transplantation for siblings with progressive familial intrahepatic cholestasis 2, with novel genetic findings," Am J Transplant. 2011, 11(2):394-398.
Simons, "The fate of the orally administered bile acid sequestrant, polidexide, in humans," Clin. Exp. Pharmacol. Physiol., 3(1):99-101, Jan.-Feb. 1976.
Singhal et al., "Drug polymorphism and dosage form design: a practical perspective," Adv Drug Deliv Rev, Feb. 23, 2004, 56(3):335-347.
Sinha and Kumria, "Microbially triggered drug delivery to the colon," Eur. J. Pharm. Sci. 2003, vol. 18, p. 3-18.
Sirtori, "Mechanisms of lipid-lowering agents," Cardiology, 78(3):226-35, 1991.
Sohn et al., "Benign Recurrent Intrahepatic Cholestasis Type 2 in Siblings with Novel ABCB11 Mutations," Pediatr Gastroenterol Hepatol Nutr. 2019, 22(2):201-206.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes *Listeria monosytogenes* colonization and translocation in rats red diets containing corn oil but not milk fat1", J. Nutrition (US) 132(6):1269-1274, 2002.
Squires et al., "Clinical Variability After Partial External Biliary Diversion in Familial Intrahepatic Cholestasis 1 Deficiency," J Pediatr Gastroenterol Nutr. 2017, 64(3):425-430.
Staels and Kuipers, "Bile acid sequestrants and the treatment of type 2 diabetes mellitus," Drugs, 67(10):1383-92, 2007.
Stein, "Managing Dyslipidemia in the High-Risk Patient," Am J. Cardiol., 2002, 89:50-57.
Sterling et al.,"Steatohepatitis: Risk factors and impact on disease severity in human immunodeficiency virus/hepatitis c virus coinfection," Hepatology, Apr. 2008, 47(4) 1118-1127.
Stindt et al., "A novel mutation within a transmembrane helix of the bile salt export pump (BSEP, ABCB11) with delayed development of cirrhosis," Liver Int. 2013, 33(10):1527-1735.
Stolz et al., "Severe and protracted cholestasis in 44 young men taking bodybuilding supplements: assessment of genetic, clinical and chemical risk factors," Aliment Pharmacol Ther. 2019, 49(9):1195-1204.
Stone et al., "Biochemical characterization of P4-ATPase mutations identified in patients with progressive familial intrahepatic cholestasis," J Biol Chem. 2012, 287(49):41139-51.
Strautnieks et al., "Severe bile salt export pump deficiency: 82 different ABCB11 mutations in 109 families," Gastroenterology. 2008, 134(4):1203-1214.
Sun et al., "Bile acids promote diethylnitrosamine-induced hepatocellular carcinoma via increased inflammatory signaling," American Journal of Physiology—Gastrointestinal and Liver Physiology, May 5, 2016, 311(1):G91-104.
Sutyagin et al., Chemistry and Physics of Polymers: Textbook.—Tomsk: TPU Publishing House, 2003, p. 132,140-143,151-152,173-174 (machine translation).
Suzuki and Takada, "Mechanisms of regulation of bile acid transport in the small intestine," Falk Symposium, 165:76-81, 2009.
Swedish Office Action for Swedish Appln. No. 1850915-8, dated Feb. 15, 2019, 6 pages.
Swedish Office Action in Swedish Appln. No. 1850761-6, dated Dec. 17, 2018, 8 pages.
Swedish Office Action in Swedish Appln. No. 1850762-4, dated Dec. 27, 2018, 7 pages.
Swedish Search Report for Swedish Appln. No. 1850915-8, dated Feb. 15, 2019, 2 pages.
Swedish Search Report in Swedish Appln. No. 1850761-6, dated Dec. 17, 2018, 3 pages.

(56) References Cited

OTHER PUBLICATIONS

Swedish Search Report in Swedish Appln. No. 1850762-4, dated Dec. 27, 2018, 3 pages.
Takahashi et al., "Gradual improvement of liver function after administration of ursodeoxycholic acid in an infant with a novel ABCB11 gene mutation with phenotypic continuum between BRIC2 and PFIC2," Eur J Gastroenterol Hepatol. 2007, 19(11):942-6.
Tanaka et al., "Genetic and Familial considerations of Primary Biliary Cirrhosis," Am. J. Gastroenterology, 2001, 96(1): 8-15.
Thakral et al., "Eudragit: a technology evaluation," Expert Opin. Drug Deliv., Jan. 2013, 10(1): 131-149.
Tian et al., "Factors affecting crystallization of hydrates," J. Pharm. Pharmacol., 2010, 62:1534-1546.
Tibesar et al., "Two Cases of Progressive Familial Intrahepatic Cholestasis Type 2 Presenting with Severe Coagulopathy without Jaundice," Case Rep Pediatr. 2014, 2014:185923.
Togawa et al., "Diversity of ATP8B1 mutations in japanese patients with intrahepatic cholestasis associated with low gamma-glutamyl transpeptidase level," Journal of Pediatric Gastroenterology and Nutrition 2018, 67(1):5363, Abstract No. 615.
Tollefson et al., "A novel class of apical sodium co-dependent bile acid transporter inhibitors: the 1,2-Benzothiazepines", Bioorganic and Medicinal Chemistry Letters 12:3727-3730, 2003.
Trauner et al., "Inflammation-induced cholestasis," J. of Gastroenterology and Hepatology, Dec. 2001, 14:10:946-959.
Treepongkaruna et al., "Novel ABCB11 mutations in a Thai infant with progressive familial intrahepatic cholestasis," World J Gastroenterol. 2009, 15(34):4339-4342.
Tremont et al., "Discovery of Potent, Nonsystemic Apical Sodium-Codependent Bile Acid Transporter Inhibitors (Part 1)," J. Med. Chem, 2005, 48:5837-5852.
Tyle, "Effect of size, shape and hardness of particles in suspension on oral texture and palatability," Acta Psychologica 1993, 84(1):111-118.
Uegaki et al., "Successful treatment with colestimide for a bout of cholestasis in a Japanese patient with benign recurrent intrahepatic cholestasis caused by ATP8B1 mutation," Intern Med. 2008, 47(7):599-602.
Van der Woerd et al., "Analysis of aberrant pre-messenger RNA splicing resulting from mutations in ATP8B1 and efficient in vitro rescue by adapted U1 small nuclear RNA," Hepatology 2015, 61(4):1382-1391.
Van der Woerd et al., "Mutational analysis of ATP8B1 in patients with chronic pancreatitis," PLoS One. 2013, 8(11):e80553.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Mil et al., "Benign recurrent intrahepatic cholestasis type 2 is caused by mutations in ABCB11," Gastroenterology. 2004, 127(2):379-384.
Van Tilberg et al., "Na+-dependent bile acid transport in the ileum: the balance between diarrhea and constipation", Gastroenterology 98(1):25-32, 1989.
Varma et al., "Retargeting of bile salt export pump and favorable outcome in children with progressive familial intrahepatic cholestasis type 2," Hepatology 2015, 62(1):198-206.
Vaz et al., "Sodium taurocholate cotransporting polypeptide (SLC10A1) deficiency: conjugated hypercholanemia without a clear clinical phenotype," Hepatology, 2015, 61(1):260-267.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
Vippagunta et al., "Crystalline solids", Advanced Drug Delivery Reviews 48:3-26, 2001.
Vitale et al., "Cryptogenic cholestasis in young and adults: ATP8B1, ABCB11, ABCB4, and TJP2 gene variants analysis by high-throughput sequencing," J Gastroenterol. 2018, 53(8):945-958.

Waisbourd-Zinman et al., "A Rare BSEP Mutation Associated with a Mild Form of Progressive Familial Intrahepatic Cholestasis Type 2," Ann Hepatol. 2017, 16(3):465-468.
Walkowiak-Tomczak, "Characteristics of plums as a raw material with valuable nutritive and dietary properties—a review," Pol. J. Food Nutr. Sci., 58(4):401-405, 2008.
Walsh et al., "Patient acceptability, safety and access: A balancing act for selecting age-appropriate oral dosage forms for paediatric and geriatric populations," Int. J. Pharm. 2017, 536(2):547-562.
Walsh et al., "Respiratory syncytial and other virus infections in persons with chronic cardiopulmonary disease," American Journal of Respiratory Critical Care Med., 1999, 160:791-795.
Wang et al., "Bile acid receptors and liver cancer," Curr. Pathobiol Rep, Mar. 2013, 1(1):29-35.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Wang et al., "Splicing analysis of rare/novel synonymous or intronic variants identified in ABCB11 heterozygotes presenting as progressive intrahepatic cholestasis with low γ-glutamyltransferase," Hepatol Res. 2018, 48(7):574-584.
Wang et al., "The Features of GGT in Patients with ATP8B1 or ABCB11 Deficiency Improve the Diagnostic Efficiency," PLoS One. 2016; 11(4):e0153114.
Watts and Illum, "Colonic Drug Delivery," Drug Development and Industrial Pharmacy, 1997, 23(9):893-913.
Welberg et al., "Calcium and the prevention of colon cancer", Scandinavian J. Gasteroenterology Suppl. 188:52-59, 1991.
What is Alagille Syndrome?,European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.
Whitington et al., "Partial external diversion of bile for the treatment of intractable pruritus associated with intrahepatic cholestasis," Gastroenterology, 95: 1, 130-136, 1988 (Abstract only).
Williams et al., Foye's Principles of Medicinal Chemistry, 5th Edition, 2002, 59-63.
Wolff, "Burger's Medicinal Chemistry, 5ed, Part I", John Wiley & Sons, 1995, pp. 975-977.
Wong et al., "Utility of oligonucleotide array-based comparative genomic hybridization for detection of target gene deletions," Clin Chem. 2008, 54(7)1141-1148.
Woolbright et al., "Novel insight into mechanisms of cholestatic liver injury," World Journal of Gastroenterology, 18: 36, 4985-4993, 2012.
Wu et al., "Discovery of a highly potent, nonabsorbable apical sodium-dependent bile acid transporter inhibitor (GSK2330672) for treatment of type 2 diabetes," J. Med. Chem., 2013, 53(12):5094-5117.
Xie et al., "Dysregulated hepatic bile acids collaboratively promote liver carcinogenesis," Int J Cancer, Oct. 15, 2016, 139(8):1764-1775.
Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zarenezhad et al., "Investigation of Common Variations of ABCB4, ATP8B1 and ABCB11 Genes in Patients with Progressive Familial Intrahepatic Cholestasis," Hepatitis Monthly: 2017, 17(2):e43500.
Zhang et al., "Abcb11 deficiency induces cholestasis coupled to impaired B-Fatty acid oxidation in mice," Journal of biological chemistry, 287: 29, 24784-2479, 2012.
Zhang et al., "Effect of bile duct ligation on bile acid composition in mouse serum and liver," Liver int, 32: 1, 58-69, 2012.
Al-Dury,"Ileal Bile Acid Transporter Inhibition for the Treatment of Chronic Constipation, Cholestatic Pruritus, and NASH," Frontiers in Pharmacology, 2018, 9:931.
Almasio et al., "Role of S-adenosyl-L-methionine in the treatment of intrahepatic cholestasis," Drugs, 1990, 40 Suppl (3):111-123.

(56) References Cited

OTHER PUBLICATIONS

Asami et al., "Treatment of children with familial hypercholesterolemia with colestilan, a newly developed bile acid-binding resin," Atherosclerosis, 2002, 164:381-2.
Baker et al. "Systematic review of progressive familial intrahepatic cholestasis," Clin Res Hepatol Gastroenterol., 2019;43:20-36.
Baringhaus, "Substrate specificity of the ileal and the hepatic Na+/bile acid cotransporters of the rabbit. II. A reliable 3D QSAR pharmacophore model for the ileal Na+/bile acid cotransporter," J. Lipid Res., 1999, 40:2158-2168.
Bull et al., "Progressive Familial Intrahepatic Cholestasis," Clin Liver Dis., Nov. 2018, 22:4:657-669.
Clinical Trials Identifier: NCT03566238, "A Double-Blind, Randomized, Placebo-Controlled, Phase 3 Study to Demonstrate Efficacy and Safety of A4250 in Children With Progressive Familial Intrahepatic Cholestasis Types 1 and 2 (PEDFIC 1)," version 24, Apr. 18, 2019, 8 pages.
Clinical Trials Identifier: NCT03659916, "Long Term Safety & Efficacy Study Evaluating The Effect of A4250 in Children With PFIC," version 11, Oct. 24, 2019, 7 pages.
Ellis et al. "Feedback regulation of human bile acid synthesis," Falk Symposium, 2005, 141:73-79.
Farmer et al., "Currently available hypolipidaemic drugs and future therapeutic developments," Baillieres Clin Endocrinol Metab, 1995, 9(4):825-47.
Fujino et al., "Pruritus in patients with chronic liver disease and serum autotaxin levels in patients with primary biliary cholangitis," BMC Gastro., 2019, 19:169.
Gillberg et al., "Clinical Pharmacology of odevixibat, a potent, selective ileal bile acid transport inhibitor with minimal systemic exposure," Annual Meeting A4250: NASPGHAN, J Pediatr Gastroenterol Nutr., 69(suppl 2):S113 Abstract No. 166-167, 2019.
Glueck, "Colestipol and probucol: treatment of primary and familial hypercholesterolemia and amelioration of atherosclerosis," Ann. Intern. Med, Apr. 1982, 96(4): 475-82.
Hofmann, "Defective Biliary Secretion during Total Parenteral Nutrition," J. Ped. Gastro. & Nutr, May 1995, 20(4):376-390.
International Search Report and Written Opinion in Appl. No. PCT/EP2021/081462, dated Jan. 1, 2022, 18 pages.
International Search Report and Written Opinion in Appln. No. PCT/EP2021/071618, dated Oct. 4, 2021, 13 pages.
Kamath et al, "Potential of ileal bile acid transporter inhibition as a therapeutic target in Alagille syndrome and progressive familial intrahepatic cholestasis," Liver int., Aug. 2020, 40:8:1812-1822.
Kremer et al., "Serum autotaxin is increased in pruritus of cholestasis, but not of other origin, and responds to therapeutic interventions," Hepatology, Oct. 2012, 56:4:1391-400.
Sangkhathat et al., "Variants Associated with Infantile Cholestatic Syndromes Detected in Extrahepatic Biliary Atresia by Whole Exome Studies: A 20-Case Series from Thailand," J. Pediatr Genet., 2018, 7:67-73.

Schonherr, "Profound Methyl Effects in Drug Discovery and a Call for New C—H Methylation Reactions," Angew. Chem. Int. Ed., 2013, 52:12256-12267.
Slavetinsky et al., "Odevixibat and partial external biliary diversion showed equal improvement of cholestasis in a patient with progressive familial intrahepatic cholestasis," BMJ Case Rep, 2020, 13:e234185.
Thebaut et al., "An update on the physiopathology and therapeutic management of cholestatic pruritus in children," Clinics and Res in Hepatology and Gastro., 2018, 42:2:103-109.
Van Wessel et al., "Genotype correlates with the natural history of severe bile salt export pump deficiency," Multicenter Study., Jul. 2020, 73:1:84-93.
Bass et al., "Inherited Disorders of Cholestasis in Adulthood," Clin. Liver. Dis., 2013, 2(5):200-203.
Charach et al., "The association of bile acid excretion and atherosclerotic coronary artery disease," Therapeutic Advances in Gastroenterology, 2011, 4(2):95-101.
Davit-Spraul et al., "Progressive familial intrahepatic cholestasis," Orphanet Journal of Rare Diseases, Jan. 2009, 4:1-12.
Garsuch et al., "Comparative investigations on different polymers for the preparation of fast-dissolving oral films," Journal of Pharmacy and Pharmacology, 2010, 62:539-545.
Gildeeva, "Polymorphism: the influence on the quality of drugs and actual methods of analysis," Kachestvennaya Klinicheskaya Praktika = Good Clinical Practice, 2017, (1):56-60 (with English abstract).
Gordienko et al., "Chemistry and Technology of Drugs and Biologically Active Compounds," Bulletin of MITHT, 2010, 5(1):93-97 (with machine translation).
Guo et al., "Serum Metabolomic Analysis of Coronary Heart Disease Patients with Stable Angina Pectoris Subtyped by Traditional Chinese Medicine Diagnostics Reveals Biomarkers Relevant to Personalized Treatments," Frontiers in Pharmacology, Jun. 2022, 12:1-14.
Khurana et al., "Bile Acids Regulate Cardiovascular Function," Clin Transl Sci, Jun. 2011, 4(3):210-218.
Mehl et al. "Liver transplantation and the management of progressive familial intrahepatic cholestasis in children," World J. Transplant, 2016, 6(2):278-90.
Parikh et al., "Batch Fluid Bed Granulation," Handbook of Pharmaceutical Granulation Technology, 2010, pp. 204-260.
PCT International Search Report and Written Opinion in International Application No. PCT/EP2021/084081, dated Jan. 27, 2022, 13 pages.
PCT International Search Report and Written Opinion in International Application No. PCT/EP2022/065165, dated Aug. 23, 2022, 9 pages.
Russian Office Action in Russian Appln. No. 2021100978, dated Dec. 20, 2022, 16 pages.
Setkina et al., "Biopharmaceutical aspects of drug technology and ways to modify bioavailability," Vestnik VSUM, 2014, 12(4):162-172 (with English abstract).
Vasavan et al., "Heart and bile acids—Clinical consequences of altered bile acid metabolism," BBA—Molecular Basis of Disease, 2018, 1864:1345-1355.

\* cited by examiner

SOLID FORMULATION AND METHOD FOR PREVENTING OR REDUCING COLORATION THEREOF

CROSS-REFERENCE TO RELATED APPLICATIONS

This application is a continuation of U.S. patent application Ser. No. 15/320,621, filed Dec. 20, 2016, which is a National Stage application under 35 U.S.C. § 371 of International Application No. PCT/JP2015/068242, filed Jun. 24, 2015, which claims the benefit of JP Application No. 2014-130092, filed Jun. 25, 2014. The disclosures of the prior applications are hereby incorporated by reference in their entirety.

TECHNICAL FIELD

The present invention relates to prevention or reduction of coloration of a solid formulation containing a benzothia(dia)zepine derivative or a pharmaceutically acceptable salt, solvate, or solvate of such a salt.

BACKGROUND ART

It is known that some benzothia(dia)zepine derivatives function as inhibitors of IBAT (Ileal Bile Acid Transporter) (Patent Document 1). The inhibitors of IBAT are useful in the treatment of dyslipidemic conditions and disorders such as hyperlipidemia, hypertriglicerridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL).

In addition, the benzothia(dia)zepine derivatives mentioned above are also useful in the treatment of functional constipation and constipation-dominant irritable bowel syndrome (C-IBS) (Patent Document 2 and Patent Document 3).

PRIOR ART DOCUMENTS

Patent Documents

Patent Document 1: Japanese Patent No. 3665055
Patent Document 2: Japanese Patent No. 4870552
Patent Document 3: Japanese Patent No. 5421326

DISCLOSURE OF INVENTION

Technical Problems

The aforementioned benzothia(dia)zepine derivatives or pharmaceutically acceptable salts, solvates, or solvates of such salts (hereinafter, simply referred to as "benzothia(dia)zepine derivative" in some cases) are stable compounds per se. For example, they are stable over time even under an atmosphere of high temperature and/or high humidity.

However, it has been found that there is a problem in that in the case of blending the aforementioned benzothia(dia)zepine derivative in a solid formulation, the benzothia(dia)zepine derivative may become unstable and coloration of the solid formulation may occur in some cases. In particular, coloration (in particular, red coloration) caused by the aforementioned benzothia(dia)zepine derivative in a solid formulation may occur even in a well-closed environment.

The present invention has an object to stabilize certain benzothia(dia)zepine derivatives in solid formulations containing the same, and provide a solid formulation containing the stabilized derivative mentioned above.

Technical Solution

The object of the present invention can be achieved, in a solid formulation containing (A) a certain benzothia(dia)zepine derivative, by not blending a combination of (b) polyethylene glycol and (C) polyvinyl alcohol, or alternatively, in the case of containing a combination of (b) polyethylene glycol and (C) polyvinyl alcohol in the aforementioned solid formulation, by isolating the aforementioned ingredient (A) from the aforementioned combination of (b) polyethylene glycol and (C) polyvinyl alcohol.

The first aspect of the present invention relates to a solid formulation characterized by comprising:

(A) a compound of formula (I) or (I'):

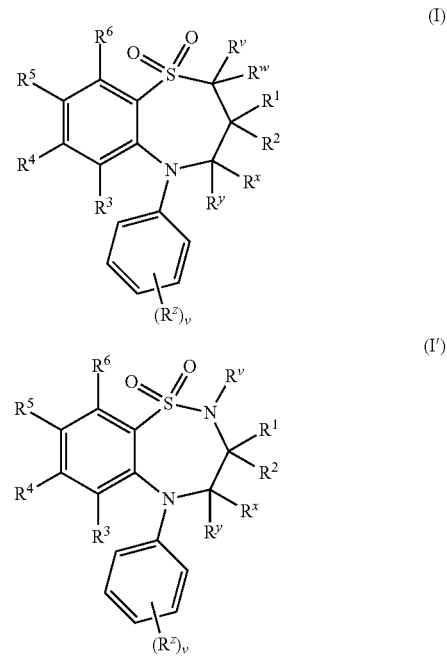

wherein:
$R^v$ and $R^w$ are independently selected from hydrogen or $C_{1-6}$ alkyl;
$R^1$ and $R^2$ are independently selected from $C_{1-6}$ alkyl;
$R^x$ and $R^y$ are independently selected from hydrogen or $C_{1-6}$ alkyl, or one of $R^x$ and $R^y$ is hydrogen or $C_{1-6}$ alkyl and the other is hydroxy or $C_{1-6}$ alkoxy;
$R^z$ is selected from halo, nitro, cyano, hydroxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$ amino, $C_{1-6}$ alkanoylamino, N—($C_{1-6}$ alkyl) carbamoyl, N,N—($C_{1-6}$ alkyl)$_2$ carbamoyl, $C_{1-6}$ alkyl S(O)$_a$ wherein a is 0 to 2, $C_{1-6}$ alkoxycarbonyl, $C_{1-6}$ alkoxycarbonylamino, ureido, N'—($C_{1-6}$ alkyl)ureido, N—($C_{1-6}$ alkyl)ureido, N',N'—($C_{1-6}$ alkyl)$_2$ ureido, N'—($C_{1-6}$ alkyl)-N—($C_{1-6}$ alkyl) ureido, N',N'—($C_{1-6}$ alkyl)$_2$-N—(C$_{1-6}$ alkyl) ureido, N—(C$_{1-6}$ alkyl) sulphamoyl and N,N—(C$_{1-6}$ alkyl)$_2$ sulphamoyl;
v is 0 to 5;
one of R$^4$ and R$^5$ is a group of formula (IA):

(IA)

R$^3$ and R$^6$, and the other of R$^4$ and R$^5$ are independently selected from hydrogen, halo, nitro, cyano, hydroxy, amino, carboxy, carbamoyl, mercapto, sulphamoyl, C$_{1-4}$ alkyl, C$_{2-4}$ alkenyl, C$_{2-4}$ alkynyl, C$_{1-4}$ alkoxy, C$_{1-4}$ alkanoyl, C$_{1-4}$ alkanoyloxy, N—(C$_{1-4}$ alkyl)amino, N,N—(C$_{1-4}$ alkyl)$_2$ amino, C$_{1-4}$ alkanoylamino, N—(C$_{1-4}$ alkyl) carbamoyl, N,N—(C$_{1-4}$ alkyl)$_2$ carbamoyl, C$_{1-4}$ alkyl S(O)$_a$ wherein a is 0 to 2, C$_{1-4}$ alkoxycarbonyl, N—(C$_{1-4}$ alkyl) sulphamoyl and N,N—(C$_{1-4}$ alkyl)$_2$ sulphamoyl; wherein R$^3$ and R$^6$ and the other of R$^4$ and R$^5$ may be optionally substituted on carbon by one or more R$^{16}$;
D is —O—, —N(R$^a$)—, —S(O)$_b$— or —CH(R$^a$)—; wherein R$^a$ is hydrogen or C$_{1-6}$ alkyl and b is 0 to 2;
Ring A is aryl or heteroaryl; wherein Ring A is optionally substituted by one or more substituents selected from R$^{17}$;
R$^7$ is hydrogen, C$_{1-4}$ alkyl, carbocyclyl or heterocyclyl; wherein R$^7$ is optionally substituted by one or more substituents selected from R$^{18}$;
R$^8$ is hydrogen or C$_{1-4}$ alkyl;
R$^9$ is hydrogen or C$_{1-4}$ alkyl;
R$^{10}$ is hydrogen, C$_{1-4}$ alkyl, carbocyclyl or heterocyclyl; wherein R$^{10}$ is optionally substituted by one or more substituents selected from R$^{19}$;
R$^{11}$ is carboxy, sulpho, sulphino, phosphono, tetrazolyl, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from C$_{1-6}$ alkyl; or R$^{11}$ is a group of formula (IB):

(IB)

wherein:
X is —N(R$^q$)—, —N(R$^q$)C(O)—, —O—, or —S(O)$_a$—; wherein a is 0 to 2 and R$^q$ is hydrogen or C$_{1-4}$ alkyl;
R$^{12}$ is hydrogen or C$_{1-4}$ alkyl;
R$^{13}$ and R$^{14}$ are independently selected from hydrogen, C$_{1-4}$ alkyl, carbocyclyl, heterocyclyl or R$^{23}$; wherein the aforementioned C$_{1-4}$ alkyl, carbocyclyl or heterocyclyl may be independently optionally substituted by one or more substituents selected from R$^{20}$;
R$^{15}$ is carboxy, sulpho, sulphino, phosphono, tetrazolyl, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from C$_{1-6}$ alkyl; or R$^{15}$ is a group of formula (IC):

(IC)

wherein:
R$^{24}$ is selected from hydrogen or C$_{1-4}$ alkyl;
R$^{25}$ is selected from hydrogen, C$_{1-4}$ alkyl, carbocyclyl, heterocyclyl or R$^{27}$; wherein said C$_{1-4}$ alkyl, carbocyclyl or heterocyclyl may be independently optionally substituted by one or more substituents selected from R$^{28}$;
R$^{26}$ is selected from carboxy, sulpho, sulphino, phosphono, tetrazolyl, —P(O)(OR$^g$)(OR$^h$), —P(O)(OH)(OR$^g$), —P(O)(OH)(R$^g$) or —P(O)(OR$^g$)(R$^h$) wherein R$^g$ and R$^h$ are independently selected from C$_{1-6}$ alkyl;
p is 1-3; wherein the meanings of R$^{13}$ may be the same or different;
q is 0-1;
r is 0-3; wherein the meanings of R$^{14}$ may be the same or different;
m is 0-2; wherein the meanings of R$^{10}$ may be the same or different;
n is 1-3; wherein the meanings of R$^7$ may be the same or different;
z is 0-3; wherein the meanings of R$^{25}$ may be the same or different;
R$^{16}$, R$^{17}$ and R$^{18}$ are independently selected from halo, nitro, cyano, hydroxy, amino, carboxy, carbamoyl, mercapto, sulphamoyl, C$_{1-4}$ alkyl, C$_{2-4}$ alkenyl, C$_{2-4}$ alkynyl, C$_{1-4}$ alkoxy, C$_{1-4}$ alkanoyl, C$_{1-4}$ alkanoyloxy, N—(C$_{1-4}$ alkyl)amino, N,N—(C$_{1-4}$ alkyl)$_2$ amino, C$_{1-4}$ alkanoylamino, N—(C$_{1-4}$ alkyl) carbamoyl, N,N—(C$_{1-4}$ alkyl)$_2$ carbamoyl, C$_{1-4}$ alkyl S(O)$_a$ wherein a is 0 to 2, C$_{1-4}$ alkoxycarbonyl, N—(C$_{1-4}$ alkyl) sulphamoyl and N,N—(C$_{1-4}$ alkyl)$_2$ sulphamoyl; wherein R$^{16}$, R$^{17}$ and R$^{18}$ may be independently optionally substituted on carbon by one or more R$^{21}$;
R$^{19}$, R$^{20}$, R$^{23}$, R$^{27}$ and R$^{28}$ are independently selected from halo, nitro, cyano, hydroxy, amino, carboxy, carbamoyl, mercapto, sulphamoyl, C$_{1-4}$ alkyl, C$_{2-4}$ alkenyl, C$_{2-4}$ alkynyl, C$_{1-4}$ alkoxy, C$_{1-4}$ alkanoyl, C$_{1-4}$ alkanoyloxy, N—(C$_{1-4}$ alkyl)amino, N,N—(C$_{1-4}$ alkyl)$_2$ amino, C$_{1-4}$ alkanoylamino, N—(C$_{1-4}$ alkyl) carbamoyl, N,N—(C$_{1-4}$ alkyl)$_2$ carbamoyl, C$_{1-4}$ alkyl S(O)$_a$ wherein a is 0 to 2, C$_{1-4}$ alkoxycarbonyl, N—(C$_{1-4}$ alkyl) sulphamoyl, N,N—(C$_{1-4}$ alkyl)$_2$ sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from C$_{1-6}$ alkyl; wherein R$^{19}$, R$^{20}$, R$^{23}$, R$^{27}$ and R$^{28}$ may be independently optionally substituted on carbon by one or more R$^{22}$;
R$^{21}$ and R$^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl, or a pharmaceutically acceptable salt, solvate, or solvate of such a salt, wherein the aforementioned solid formulation is free from a combination of (b) polyethylene glycol and (C) polyvinyl alcohol, or alternatively, in the case of containing a combination of (b) polyethylene glycol and (C) polyvinyl alcohol in the aforementioned solid formulation, the aforementioned ingredient (A) is isolated from the aforementioned combination of (b) polyethylene glycol and (C) polyvinyl alcohol.

The aforementioned solid formulation preferably contains:

at least one core, and at least one coating layer or capsule layer enclosing at least a part of said core, and the aforementioned coating layer or capsule layer is free from a combination of (b) polyethylene glycol and (C) polyvinyl alcohol, or alternatively in the case of the aforementioned coating layer or capsule layer containing a combination of (b) polyethylene glycol and (C) polyvinyl alcohol, at least one isolation layer is provided between the aforementioned core and the aforementioned coating layer or capsule layer.

The aforementioned core preferably contains the aforementioned ingredient (A).

The coating layer or capsule layer can be present in a ratio ranging from 1 to 20% by weight based on the total weight of the solid formulation. In the present specification, the term "weight" has the same meaning as that of "mass". Therefore, "% by weight" and "part (s) by weight" have the same meanings as those of "% by mass" and "part(s) by mass", respectively.

The aforementioned coating layer or capsule layer can contain the aforementioned ingredient (b) in an amount ranging from 0.1 to 50% by weight based on the total weight of the coating layer or capsule layer.

The aforementioned coating layer or capsule layer may contain the aforementioned ingredient (C) in an amount ranging from 50 to 90% by weight based on the total weight of the coating layer or capsule layer.

The coating layer or capsule layer preferably further contains at least one selected from the group consisting of a water-soluble polymer other than polyethylene glycol and polyvinyl alcohol, a colorant, a lubricant, and wax.

The water-soluble polymer is preferably hydroxypropyl methylcellulose.

The colorant is preferably selected from the group consisting of titanium oxide, iron oxide, zinc oxide, tar pigment, and lake pigment.

The lubricant is preferably talc.

The wax is preferably carnauba wax.

The core preferably contains at least one additive selected from the group consisting of a filler, a disintegrant, a binder, a lubricant, and a fluidizer.

The solid formulation according to the present invention is preferably a film-coated tablet or a capsule.

The aforementioned ingredient (A) is preferably selected from the group consisting of:

1,1-dioxo-3,3-dibutyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine; and 1,1-dioxo-3,3-dibutyl-5-phenyl-7-methylthio-8-(N—{(R)-1'-phenyl-1'-[N'-(carboxymethyl)carbamoyl] methyl}carbamoylmethoxy)-2,3,4,5-tetrahydro-1,5-benzothiazepine.

The aforementioned ingredient (A) is more preferably 1,1-dioxo-3,3-dibutyl-5-phenyl-7-methylthio-8-(N—{(R)-1'-phenyl-1'-[N'-(carboxymethyl)carbamoyl] methyl}carbamoylmethoxy)-2,3,4,5-tetrahydro-1,5-benzothiazepine, that is, Elobixibat.

The amount of the aforementioned ingredient (A) may range from 0.01 to 50% by weight based on the total weight of the solid formulation.

The amount of the aforementioned ingredient (A) may range from 1 to 20 mg.

The aforementioned polyethylene glycol preferably has an average molecular weight ranging from 200 to 20,000.

The solid formulation according to the present invention is preferably in the form of a tablet having a diameter ranging from 5 to 11 mm.

The solid formulation according to the present invention is preferably intended for treating or preventing constipation in a warm-blooded animal including a human being. The aforementioned constipation may be functional constipation or constipation-predominant irritable bowel syndrome.

The second aspect of the present invention relates to a method for preventing or reducing coloration of a solid formulation containing (A) a compound of formula (I) or (I'), or a pharmaceutically acceptable salt, solvate, or solvate of such a salt, characterized in that a combination of (b) polyethylene glycol and (C) polyvinyl alcohol is not added to the aforementioned solid formulation, or alternatively, in the case of adding a combination of (b) polyethylene glycol and (C) polyvinyl alcohol to the aforementioned solid formulation, the aforementioned ingredient (A) is isolated from the aforementioned combination of (b) polyethylene glycol and (C) polyvinyl alcohol.

Effects of the Invention

In accordance with the present invention, a certain benzothia(dia)zepine derivative in a solid formulation containing the same can be stabilized, and a solid formulation containing the stabilized derivative can be provided.

The benzothia(dia)zepine derivatives in the solid formulations according to the present invention are stable over time even under an atmosphere at high temperature and/or in high moisture. Therefore, even if the solid formulations according to the present invention are allowed to stand under an atmosphere at high temperature and/or in high moisture, occurrence of coloration (in particular, red coloration phenomenon) of the solid formulations derived due to destabilization of the benzothia(dia)zepine derivatives mentioned above can be prevented or reduced. In particular, the solid formulations of the present invention are stable under well-closed environment.

Therefore, the solid formulations of the present invention can be stored for a long period of time, and the pharmaceutical effects of the benzothia(dia)zepine derivatives contained in the solid formulations can be maintained. In particular, the solid formulations of the present invention can be stable even under an atmosphere at high temperature and/or in high moisture in the summer season.

MODE FOR CARRYING OUT THE INVENTION

As a result of diligent studies of the cause of destabilization of the aforementioned benzothia(dia)zepine derivatives (in particular, red coloration phenomenon) in solid formulations containing the derivatives mentioned above, the inventors of the present application determined the cause. That is, the aforementioned benzothia(dia)zepine derivatives contact a combination of polyethylene glycol and polyvinyl alcohol in the solid formulations, thus causing destabilization of the derivatives.

In the present invention, in a solid formulation containing the aforementioned benzothia(dia)zepine derivative, a combination of polyethylene glycol and polyvinyl alcohol is not added to the solid formulation, or alternatively, in the case of adding a combination of polyethylene glycol and polyvinyl alcohol to the solid formulation, the benzothia(dia)zepine derivative is isolated from the combination of polyethylene glycol and polyvinyl alcohol, thus preventing or reducing destabilization of the benzothia(dia)zepine derivative. Thereby, coloration of the solid formulation derived due to destabilization of the aforementioned benzothia(dia)zepine derivative can be prevented or reduced.

Hereinafter, the embodiments for carrying out the present invention are described in detail.

A first aspect of the present invention relates to a solid formulation containing a certain benzothia(dia)zepine derivative, wherein the solid formulation is free from a combination of polyethylene glycol and polyvinyl alcohol, or alternatively, in the case of containing a combination of polyethylene glycol and polyvinyl alcohol in the solid formulation, the aforementioned benzothia(dia)zepine derivative is isolated from the combination of polyethylene glycol and polyvinyl alcohol.

The benzothia(dia)zepine derivatives usable in the present invention are preferably (A) compounds represented by the following formula (I) or (I'):

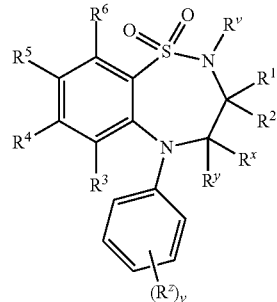

(I)

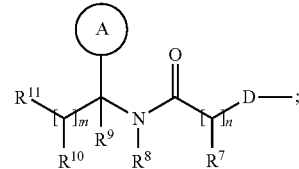

(I')

wherein:
$R^v$ and $R^w$ are independently selected from hydrogen or $C_{1-6}$ alkyl;
$R^1$ and $R^2$ are independently selected from $C_{1-6}$ alkyl;
$R^x$ and $R^y$ are independently selected from hydrogen or $C_{1-6}$ alkyl, or one of $R^x$ and $R^y$ is hydrogen or $C_{1-6}$ alkyl and the other is hydroxy or $C_{1-6}$ alkoxy;
$R^z$ is selected from halo, nitro, cyano, hydroxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$ amino, $C_{1-6}$ alkanoylamino, N—($C_{1-6}$ alkyl) carbamoyl, N,N—($C_{1-6}$ alkyl)$_2$ carbamoyl, $C_{1-6}$ alkyl $S(O)_a$ wherein a is 0 to 2, $C_{1-6}$ alkoxycarbonyl, $C_{1-6}$ alkoxycarbonylamino, ureido, N'—($C_{1-6}$ alkyl)ureido, N—($C_{1-6}$ alkyl)ureido, N',N'—($C_{1-6}$ alkyl)$_2$ ureido, N'—($C_{1-6}$ alkyl)-N—($C_{1-6}$ alkyl) ureido, N',N'—($C_{1-6}$ alkyl)$_2$-N—($C_{1-6}$ alkyl) ureido, N—($C_{1-6}$ alkyl) sulphamoyl and N,N—($C_{1-6}$ alkyl)$_2$ sulphamoyl;
v is 0 to 5;
one of $R^4$ and $R^5$ is a group of formula (IA):

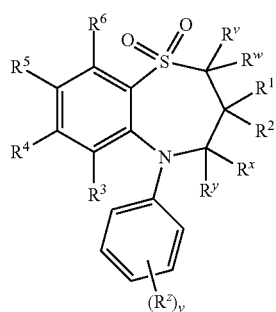

(IA)

$R^3$ and $R^6$, and the other of $R^4$ and $R^5$ are independently selected from hydrogen, halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl) carbamoyl, N,N—($C_{1-4}$ alkyl)$_2$ carbamoyl, $C_{1-4}$ alkyl $S(O)_a$ wherein a is 0 to 2, $C_{1-4}$ alkoxycarbonyl, N—($C_{1-4}$ alkyl) sulphamoyl and N,N—($C_{1-4}$ alkyl)$_2$ sulphamoyl; wherein $R^3$ and $R^6$ and the other of $R^4$ and $R^5$ may be optionally substituted on carbon by one or more $R^{16}$;
D is —O—, —N($R^a$)—, —S(O)$_b$— or —CH($R^a$)—; wherein $R^a$ is hydrogen or $C_{1-6}$ alkyl and b is 0 to 2;
Ring A is aryl or heteroaryl; wherein Ring A is optionally substituted by one or more substituents selected from $R^{17}$;
$R^7$ is hydrogen, $C_{1-4}$ alkyl, carbocyclyl or heterocyclyl; wherein $R^7$ is optionally substituted by one or more substituents selected from $R^{18}$;

$R^8$ is hydrogen or $C_{1-4}$ alkyl;
$R^9$ is hydrogen or $C_{1-4}$ alkyl;
$R^{10}$ is hydrogen, $C_{1-4}$ alkyl, carbocyclyl or heterocyclyl; wherein $R^{10}$ is optionally substituted by one or more substituents selected from $R^{19}$;
$R^{11}$ is carboxy, sulpho, sulphino, phosphono, tetrazolyl, —P(O))(OR$^c$)(OR$^d$), —P(O)(OH))(OR$^c$), —P(O)(OH)(R$^d$) or —P(O)(OR$^c$)(R$^d$) wherein R$^c$ and R$^d$ are independently selected from $C_{1-6}$ alkyl; or $R^{11}$ is a group of formula (IB):

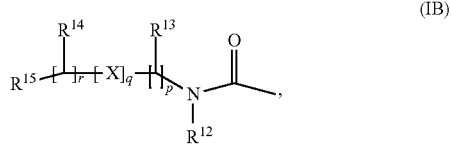

wherein:
X is —N(R$^q$)—, —N(R$^q$)C(O)—, —O—, or —S(O)$_a$—; wherein a is 0 to 2 and R$^q$ is hydrogen or $C_{1-4}$ alkyl;
$R^{12}$ is hydrogen or $C_{1-4}$ alkyl;
$R^{13}$ and $R^{14}$ are independently selected from hydrogen, $C_{1-4}$ alkyl, carbocyclyl, heterocyclyl or $R^{23}$; wherein said $C_{1-4}$ alkyl, carbocyclyl or heterocyclyl may be independently optionally substituted by one or more substituents selected from $R^{20}$;
$R^{15}$ is carboxy, sulpho, sulphino, phosphono, tetrazolyl, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$ alkyl; or $R^{15}$ is a group of formula (IC):

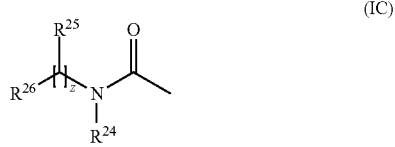

wherein:
$R^{24}$ is selected from hydrogen or $C_{1-4}$ alkyl;
$R^{25}$ is selected from hydrogen, $C_{1-4}$ alkyl, carbocyclyl, heterocyclyl or $R^{27}$; wherein said $C_{1-4}$ alkyl, carbocyclyl or heterocyclyl may be independently optionally substituted by one or more substituents selected from $R^{28}$;
$R^{26}$ is selected from carboxy, sulpho, sulphino, phosphono, tetrazolyl, —P(O)(OR$^g$)(OR$^h$), —P(O)(OH)(OR$^g$), —P(O)(OH)(R$^g$) or —P(O)(OR$^g$)(R$^h$) wherein R$^g$ and R$^h$ are independently selected from $C_{1-6}$ alkyl;
p is 1-3; wherein the meanings of $R^{13}$ may be the same or different;
q is 0-1;
r is 0-3; wherein the meanings of $R^{14}$ may be the same or different;
m is 0-2; wherein the meanings of $R^{10}$ may be the same or different;
n is 1-3; wherein the meanings of $R^7$ may be the same or different;
z is 0-3; wherein the meanings of $R^{25}$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl) carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)$_2$ sulphamoyl; wherein $R^{16}$, $R^{17}$ and $R^{18}$ may be independently optionally substituted on carbon by one or more $R^{21}$;
$R^{19}$, $R^{20}$, $R^{23}$, $R^{27}$ and $R^{28}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl) carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl, N,N—($C_{1-4}$ alkyl)$_2$ sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$ alkyl; wherein $R^{19}$, $R^{20}$, $R^{23}$, $R^{27}$ and $R^{28}$ may be independently optionally substituted on carbon by one or more $R^{22}$;
$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl,
or a pharmaceutically acceptable salt, solvate, or solvate of such a salt; or alternatively a prodrug of the same (hereinafter, simply referred to as "ingredient (A)" in some cases).

The compound of the aforementioned formula (I) is preferably a compound represented by the following formula (I-1):

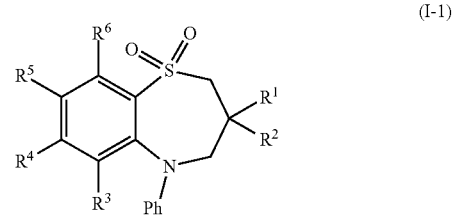

wherein
$R^1$ and $R^2$ are independently selected from $C_{1-6}$ alkyl;
one of $R^4$ and $R^5$ is a group of the following formula (I-1A'):

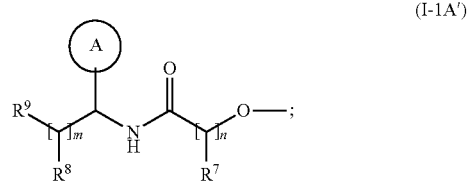

R³ and R⁶, and the other of R⁴ and R⁵ are independently selected from hydrogen, halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)₂ amino, $C_{1-4}$ alkanoylamino, N—($C_{1-4}$ alkyl) carbamoyl, N,N—($C_{1-4}$ alkyl)₂ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)₂ sulphamoyl; wherein R³ and R⁶ and the other of R⁴ and R⁵ may be optionally substituted on carbon by one or more $R^{12}$;

Ring A is aryl or heteroaryl; wherein Ring A is optionally substituted by one or more substituents selected from $R^{13}$;

R⁷ is hydrogen, $C_{1-4}$ alkyl, carbocyclyl or heterocyclyl; wherein R⁷ is optionally substituted by one or more substituents selected from $R^{14}$;

R⁸ is hydrogen, $C_{1-4}$ alkyl, carbocyclyl or heterocyclyl; wherein R⁸ is optionally substituted by one or more substituents selected from $R^{15}$;

R⁹ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$ alkyl; or R⁹ is a group of formula (I-1B'):

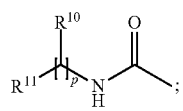

wherein:
$R^{10}$ is selected from hydrogen, $C_{1-4}$ alkyl, carbocyclyl or heterocyclyl; wherein $R^{10}$ may be independently optionally substituted by one or more substituents selected from $R^{16}$;

$R^{11}$ is selected from carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$ alkyl;

p is 1-3; wherein the meanings of $R^{10}$ may be the same or different;

m is 0-2; wherein the meanings of R³ may be the same or different;

n is 1-3; wherein the meanings of R⁷ may be the same or different;

$R^{12}$, $R^{13}$ and $R^{14}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)₂ amino, $C_{1-4}$ alkanoylamino, N—($C_{1-4}$ alkyl) carbamoyl, N,N—($C_{1-4}$ alkyl)₂ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)₂ sulphamoyl;

wherein $R^{12}$, $R^{13}$ and $R^{14}$ may be independently optionally substituted on carbon by one or more $R^{12}$;

$R^{15}$ and $R^{16}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)₂ amino, $C_{1-4}$ alkanoylamino, N—($C_{1-4}$ alkyl) carbamoyl, N,N—($C_{1-4}$ alkyl)₂ carbamoyl, $C_{1-4}$ alkyl S(O)$_a$ wherein a is 0 to 2, $C_{1-4}$ alkoxycarbonyl, N—($C_{1-4}$ alkyl) sulphamoyl, N,N—($C_{1-4}$ alkyl)₂ sulphamoyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$ alkyl; wherein $R^{15}$ and $R^{16}$ may be independently optionally substituted on carbon by one or more $R^{18}$;

$R^{17}$ and $R^{18}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl.

The compound of the aforementioned formula (I) is more preferably a compound represented by the following formula (I-2):

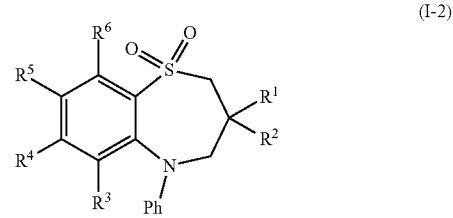

wherein
R¹ and R² are independently selected from $C_{1-6}$ alkyl;
one of R⁴ and R⁵ is a group of the following formula (I-2A"):

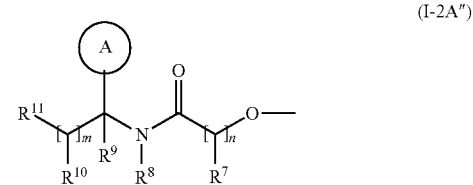

R³ and R⁶, and the other of R⁴ and R⁵ are independently selected from hydrogen, halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)₂ amino, $C_{1-4}$ alkanoylamino, N—($C_{1-4}$ alkyl) carbamoyl, N,N—($C_{1-4}$ alkyl)₂ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)₂ sulphamoyl; wherein R³ and R⁶ and the other of R⁴ and R⁵ may be optionally substituted on carbon by one or more $R^{16}$;

Ring A is aryl or heteroaryl; wherein Ring A is optionally substituted by one or more substituents selected from $R^{17}$;

R⁷ is hydrogen, $C_{1-4}$ alkyl, carbocyclyl or heterocyclyl; wherein R⁷ is optionally substituted by one or more substituents selected from $R^{18}$;

R⁸ is hydrogen or $C_{1-4}$ alkyl;
R⁹ is hydrogen or $C_{1-4}$ alkyl;

$R^{10}$ is hydrogen, $C_{1-4}$ alkyl, carbocyclyl or heterocyclyl; wherein $R^{10}$ is optionally substituted by one or more substituents selected from $R^{19}$;

$R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$ alkyl; or $R^{11}$ is a group of formula (I-2B″):

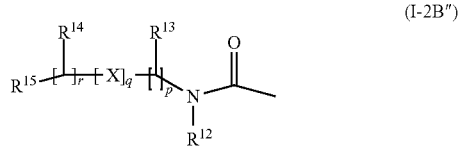

wherein

X is —N(R$^q$)—, —N(R$^q$)C(O)—, —O—, or —S(O)$_a$— wherein a is 0 to 2 and R$^q$ is hydrogen or $C_{1-4}$ alkyl;

$R^{12}$ is hydrogen or $C_{1-4}$ alkyl;

$R^{13}$ and $R^{14}$ are independently selected from hydrogen, $C_{1-4}$ alkyl, carbocyclyl or heterocyclyl; wherein $R^{13}$ and $R^{14}$ are optionally substituted by one or more substituents selected from $R^{20}$;

$R^{15}$ is carboxy, sulpho, sulphino, phosphono, —P(O)(OR$^e$)(OR$^f$), —P(O)(OH)(OR$^e$), —P(O)(OH)(R$^e$) and —P(O)(OR$^e$)(R$^f$) wherein R$^e$ and R$^f$ are independently selected from $C_{1-6}$ alkyl;

p is 1-3; wherein the meanings of $R^{13}$ may be the same or different;

q is 0-1;

r is 0-3; wherein the meanings of $R^{14}$ may be the same or different;

m is 0-2; wherein the meanings of $R^{10}$ may be the same or different;

n is 1-3; wherein the meanings of $R^7$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl) carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)$_2$ sulphamoyl;

wherein $R^{16}$, $R^{17}$ and $R^{18}$ may be independently optionally substituted on carbon by one or more $R^{21}$;

$R^{19}$ and $R^{20}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl) carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl, N,N—($C_{1-4}$ alkyl)$_2$ sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$ alkyl; wherein $R^{19}$ and $R^{20}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl.

Hereinafter, in the case of indicating a compound of formula (I), it should be understood that the aspect thereof also relates to the compounds of formula (I-1) and the compounds of formula (I-2).

In addition, a person having ordinary skill in the art will recognize that the numbering system differs between the compounds of formula (I) and the compounds of formula (I-1). The numbering system used hereinafter in the present specification refers to the compounds of formula (I). However, it should be understood that such a numbering system is also applied to the meanings corresponding to those of formula (I-1).

In the present specification, the term "alkyl" includes both straight and branched chain alkyl groups, but the references to individual alkyl groups such as "propyl" are specific for the straight chain version only. For example, "$C_{1-6}$ alkyl" includes $C_{1-4}$ alkyl, $C_{1-3}$ alkyl, propyl, isopropyl and t-butyl. However, references to individual alkyl groups such as 'propyl' are specific for the straight-chain version only and references to individual branched chain alkyl groups such as 'isopropyl' are specific for the branched chain version only. A similar convention applies to other radicals, for example "phenyl $C_{1-6}$ alkyl" would include phenyl $C_{1-4}$ alkyl, benzyl, 1-phenylethyl and 2-phenylethyl. The term "halo" refers to fluoro, chloro, bromo and iodo.

In the case where optional substituents are chosen from "one or more" groups, it should be understood that such a definition includes all substituents being chosen from one of the specified groups or chosen from two or more of the specified groups.

"Heteroaryl" is a totally unsaturated, monocyclic or bicyclic ring containing 3-12 atoms of which at least one atom is chosen from nitrogen, sulfur or oxygen, and which may, unless otherwise specified, be carbon- and nitrogen-linked. A preferable "heteroaryl" refers to a totally unsaturated, monocyclic ring containing 5 or 6 atoms or a totally unsaturated, bicyclic ring containing 9 or 10 atoms of which at least one atom is chosen from nitrogen, sulfur and oxygen, and which may, unless otherwise specified, be carbon- or nitrogen-linked. In another aspect of the present invention, "heteroaryl" refers to a totally unsaturated, monocyclic ring containing 5 or 6 atoms or a totally unsaturated, bicyclic ring containing 8, 9 or 10 atoms of which at least one atom is chosen from nitrogen, sulfur and oxygen, and which may, unless otherwise specified, be carbon- or nitrogen-linked. Examples and suitable meanings of the term "heteroaryl" are thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl and quinolyl. The term "heteroaryl" preferably refers to thienyl or indolyl.

"Aryl" is a totally unsaturated, mono or bicyclic carbon ring that contains 3-12 atoms. Preferable "aryl" is a monocyclic ring containing 5 or 6 atoms or a bicyclic ring containing 9 or 10 atoms. Suitable meanings for "aryl" include phenyl or naphthyl. "Aryl" is more preferably phenyl.

"Heterocyclyl" is a saturated, partially saturated or unsaturated, mono or bicyclic ring containing 3-12 atoms of which at least one atom is chosen from nitrogen, sulfur and oxygen, and which may, unless otherwise specified, be carbon- or nitrogen-linked, wherein a —CH$_2$— group can optionally be replaced by a —C(O)—, or a ring sulfur atom may be optionally oxidized to form S-oxide. Preferably "heterocyclyl" is a saturated, partially saturated or unsaturated, mono or bicyclic ring containing 5 or 6 atoms of which at least one atom is chosen from nitrogen, sulfur and oxygen, and which may, unless otherwise specified, be carbon- or nitrogen-linked, wherein a —CH$_2$— group can optionally be replaced by a —C(O)— or a ring sulfur atom may be optionally oxidized to form S-oxide(s). Examples and suitable meanings of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrinidyl, thiazolyl, pyrazinyl, pyridazinyl, pyridyl, 4-pyridonyl, quinolyl and 1-isoquinolonyl.

"Carbocyclyl" is a saturated, partially saturated or unsaturated, mono or bicyclic carbon ring that contains 3-12 atoms; wherein a —CH$_2$— group can optionally be replaced by a —C(O)—. Preferable "carbocyclyl" is a monocyclic ring containing 5 or 6 atoms or a bicyclic ring containing 9 or 10 atoms. Suitable meanings for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. In particular, "carbocyclyl" is cyclopropyl, cyclobutyl, 1-oxocyclopentyl, cyclopentyl, cyclopentenyl, cyclohexyl, cyclohexenyl, phenyl or 1-oxoindanyl.

An example of "$C_{1-6}$ alkanoyloxy" and "$C_{1-4}$ alkanoyloxy" is acetoxy. Examples of "$C_{1-6}$ alkoxycarbonyl" and "$C_{1-4}$ alkoxycarbonyl" include methoxycarbonyl, ethoxycarbonyl, and n- and t-butoxycarbonyl. Examples of "$C_{1-6}$ alkoxy" and "$C_{1-4}$ alkoxy" include methoxy, ethoxy and propoxy. Examples of "$C_{1-6}$ alkanoylamino" and "$C_{1-4}$ alkanoylamino" include formamido, acetamido and propionylamino. Examples of "$C_{1-6}$ alkyl S(O)$_a$ wherein a is 0 to 2" and "$C_{1-4}$ alkyl S(O)$_a$ wherein a is 0 to 2" include methylthio, ethylthio, methylsulphinyl, ethylsulphinyl, mesyl and ethylsulphonyl. Examples of "$C_{1-6}$ alkanoyl" and "$C_{1-4}$ alkanoyl" include $C_{1-3}$ alkanoyl, propionyl and acetyl. Examples of "N—($C_{1-6}$ alkyl)amino" and "N—($C_{1-4}$ alkyl)amino" include methylamino and ethylamino. Examples of "N,N—($C_{1-6}$ alkyl)$_2$ amino" and "N,N—($C_{1-4}$ alkyl)$_2$ amino" include di-N-methylamino, di-(N-ethyl)amino and N-ethyl-N-methylamino. Examples of "$C_{2-6}$ alkenyl" and "$C_{2-4}$ alkenyl" are vinyl, allyl and 1-propenyl. Examples of "$C_{2-6}$ alkynyl" and "$C_{2-4}$ alkynyl" are ethynyl, 1-propynyl and 2-propynyl. Examples of "N—($C_{1-6}$alkyl)sulphamoyl" and "N—($C_{1-4}$ alkyl)sulphamoyl" are N—($C_{1-3}$ alkyl)sulphamoyl, N-(methyl)sulphamoyl and N-(ethyl)sulphamoyl. Examples of "N—($C_{1-6}$ alkyl)$_2$ sulphamoyl" and "N—($C_{1-4}$ alkyl)$_2$ sulphamoyl" are N,N-(dimethyl)sulphamoyl and N-(methyl)-N-(ethyl)sulphamoyl. Examples of "N—($C_{1-6}$ alkyl)carbamoyl" and "N—($C_{1-4}$ alkyl)carbamoyl" are methylaminocarbonyl and ethylaminocarbonyl. Examples of "N,N—($C_{1-6}$ alkyl)$_2$ carbamoyl" and "N,N—($C_{1-4}$ alkyl)$_2$ carbamoyl" are dimethylaminocarbonyl and methylethyl-aminocarbonyl. Examples of "$C_{1-6}$ alkoxycarbonylamino" are ethoxycarbonylamino and t-butoxycarbonylamino. Examples of "N'—($C_{1-6}$ alkyl) ureido" are N'-methylureido and N'-ethylureido. Examples of "N—($C_{1-6}$ alkyl)ureido" are N-methylureido and N-ethylureido. Examples of "N', N'—($C_{1-6}$ alkyl)$_2$ ureido" are N',N'-dimethylureido and N'-methyl-N'-ethylureido. Examples of "N—($C_{1-6}$ alkyl)-N—($C_{1-6}$ alkyl)ureido" are N'-methyl-N-methylureido and N'-propyl-N-methylureido. Examples of "N',N'—($C_{1-6}$ alkyl)$_2$-N($C_{1-6}$ alkyl)ureido" are N',N'-dimethyl-N-methylureido and N'-methyl-N'-ethyl-N-propylureido.

A suitable pharmaceutically acceptable salt of the compound of the present invention mentioned above is, for example, an acid-addition salt of a compound of the present invention which is sufficiently basic, such as an acid-addition salt with, for example, an inorganic or organic acid, such as hydrochloric acid, hydrobromic acid, sulphuric acid, phosphoric acid, trifluoroacetic acid, citric acid or maleic acid. In addition, a suitable pharmaceutically acceptable salt of a compound of the present invention which is sufficiently acidic is an alkali metal salt such as a sodium or potassium salt, an alkaline earth metal salt such as a calcium or magnesium salt, an ammonium salt or a salt with an organic base which affords a physiologically-acceptable cation, for example, a salt with methylamine, dimethylamine, trimethylamine, piperidine, morpholine or tris-(2-hydroxyethyl)amine.

The compounds of formula (I) may be administered in the form of a pro-drug which is decomposed in the human or animal body to give a compound of formula (I). Examples of pro-drugs include in vivo hydrolysable esters and in vivo hydrolysable amides of a compound of formula (I).

An in vivo hydrolysable ester of a compound of formula (I) containing a carboxy or hydroxy group is, for example, a pharmaceutically acceptable ester which is hydrolyzed in the human or animal body to produce the parent acid or alcohol. Suitable pharmaceutically acceptable esters for carboxy include $C_{1-6}$ alkoxymethyl esters such as methoxymethyl, $C_{1-6}$ alkanoyloxymethyl esters such as pivaloyloxymethyl, phthalidyl esters, $C_{3-8}$ cycloalkoxycarbonyloxy $C_{1-6}$ alkyl esters such as 1-cyclohexylcarbonyloxyethyl; 1,3-dioxolen-2-onylmethyl esters such as 5-methyl-1,3-dioxolen-2-onylmethyl; and $C_{1-6}$ alkoxycarbonyloxyethyl esters such as 1-methoxycarbonyloxyethyl, and may be formed at any carboxy group in the compounds of the present invention.

An in vivo hydrolysable ester of a compound of formula (I) containing a hydroxy group includes inorganic esters such as phosphate esters and alpha-acyloxyalkyl ethers and related compounds which as a result of the in vivo hydrolysis of the ester decomposed to give the parent hydroxy group. Examples of alpha-acyloxyalkyl ethers include acetoxymethoxy and 2,2-dimethylpropionyloxy-methoxy. A selection of in vivo hydrolysable ester-forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Examples of substituents on benzoyl include morpholino and piperazino linked from a ring nitrogen atom via a methylene group to the 3- or 4-position of the benzoyl ring.

A suitable meaning for an in vivo hydrolysable amide of a compound of formula (I) containing a carboxy group is, for example, an N—$C_{1-6}$ alkyl or N,N-di-$C_{1-6}$ alkyl amide such as N-methyl, N-ethyl, N-propyl, N,N-dimethyl, N-ethyl-N-methyl or N,N-diethyl amide.

The compounds mentioned above have IBAT inhibitory activities. Some compounds of formula (I) may have chiral centers and/or geometric isomeric centers (E- and Z-isomers), and it should be understood that the present invention encompasses all such optical, diastereoisomers and geometric isomers that possess IBAT inhibitory activities.

The aforementioned ingredient (A) in the present invention relates to any and all tautomeric forms of the compounds of formula (I) that possess IBAT inhibitory activities.

It should also be understood that certain compounds of formula (I) can exist in the solvated as well as unsolvated forms such as a hydrated form. It should be understood that the ingredient (A) mentioned above in the present invention encompasses all such solvated forms which possess IBAT inhibitory activities.

More preferable compounds as a compound of formula (I) are represented by the following formula (I-3):

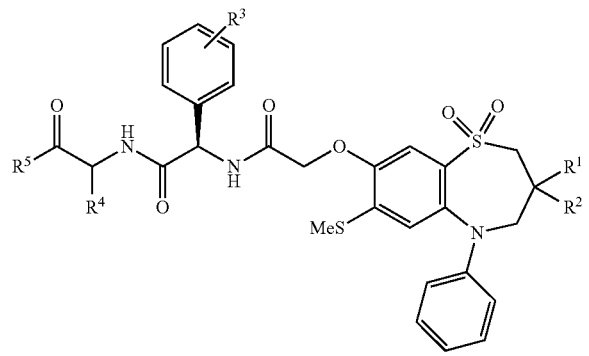

(I-3)

wherein:
R$^1$ and R$^2$ are independently selected from C$_{1-4}$ alkyl;
R$^3$ is hydrogen, hydroxy or halo;
R$^4$ is hydrogen or C$_{1-4}$ alkyl which may be substituted by hydroxy, methoxy and methyl S(O)$_a$ wherein a is 0 to 2;
R$^5$ is hydroxy or HOC(O)CH(R$^6$)NH—;
R$^6$ is selected from hydrogen and C$_{1-3}$ alkyl which may be substituted by hydroxy, methoxy and methyl S(O)$_a$ wherein a is 0 to 2;
with the proviso that in the case where both R$^1$ and R$^2$ are butyl, R$^5$ is hydroxy, and R$^4$ is methylthiomethyl, methylsulfinylmethyl, 2-methylthioethyl, hydroxymethyl, or methoxymethyl, R$^3$ is not hydrogen; and with the proviso that in the case where both R$^1$ and R$^2$ are butyl, R$^5$ is HOC(O)CH(R$^6$)NH—, and R$^6$ is hydroxymethyl, and R$^4$ is hydroxymethyl, R$^3$ is not hydrogen.

As the compound of formula (I), in particular, 1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiadiazepine, that is, Elobixibat is preferable.

On the other hand, as the compound of formula (I'), in particular, 1,1-dioxo-3,3-dibutyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine; or 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine is preferable.

A compound of formula (I) or (I'), or a pharmaceutically acceptable salt, solvate, solvate of such a salt or a prodrug thereof can be manufactured in accordance with a method described in, for example, Japanese Patent No. 3665005 (the content of which is incorporated in the specification of the present application by reference).

The aforementioned ingredient (A) possesses IBAT inhibitory activities. These properties may be assessed, for example, using an in vitro test assay for studying the effect on bile acid uptake in IBAT-transfected cells (Smith L., Price-Jones M. J., Hugnes K. T., and Jones N. R. A.; J Biomolecular Screening, 3, 227-230) or in vivo by studying the effect on radiolabelled bile acid absorption in mice/rats (Lewis M. C., Brieaddy L. E. and Root C., J., J Lip Res 1995, 36, 1098-1105).

The aforementioned ingredient can be used in the treatment of dyslipidemic conditions and disorders such as hyperlipidemia, hypertriglyceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as a human being.

In addition, the aforementioned ingredient (A) can be used in the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocyte, monocytes and/or macrophage infiltrate, intimital thickening, medial thinning, infectious and surgical trauma and vascular thrombosis, stroke and transient ischemic attacks in a warm-blooded animal, such as a human being.

There is evidence indicating that an IBAT inhibitor can be potentially useful in the treatment and/or prevention of gallstone or cholelithiasis. The aforementioned ingredient (A) can be used in the treatment and/or prevention of gallstone or cholelithiasis in a warm-blooded animal, such as a human being.

In the present invention, the aforementioned ingredient (A) can also be used in the treatment of gastrointestinal disorders. In particular, the ingredient (A) can be used in the treatment of chronic constipation, functional constipation and irritable bowel syndrome, and in particular, constipation-dominant irritable bowel syndrome (C-IBS).

In the specification of the present application, in the case of using the terms "functional constipation" and "C-IBS", it should be understood that they are defined in accordance with "Rome 2 Criteria" (Gut 45 (Suppl 2): 43, 1999, 1143-1147).

An amount of the aforementioned ingredient (A) contained in the solid formulation of the present invention is not particularly limited, and can range from 0.01 to 50% by weight, preferably ranges from 0.05 to 40% by weight, more preferably ranges from 0.1 to 30% by weight, even more preferably ranges from 0.2 to 20% by weight, even more preferably ranges from 0.5 to 10% by weight, and in particular, preferably ranges from 0.8 to 5% by weight, based on the total weight of the solid formulation.

An amount of the aforementioned ingredient (A) contained in the solid formulation of the present invention is not particularly limited, and can range from 0.1 to 100 mg, preferably ranges from 0.3 to 75 mg, more preferably ranges from 0.5 to 50 mg, even more preferably ranges from 0.8 to 30 mg, and in particular, preferably ranges from 1 to 20 mg.

Polyethylene glycol (b) (hereinafter, simply referred to as "ingredient (b)" in some cases) in the first aspect of the present invention has an average molecular weight preferably ranging from 200 to 20,000, more preferably ranging from 300 to 10,000, and even more preferably ranging from 400 to 6,000. The average molecular weight used herein may be a number average molecular weight.

Polyvinyl alcohol (C) (hereinafter, simply referred to as "ingredient (C)" in some cases) in the first aspect of the present invention is not particularly limited as long as it can be usually used for film-coating a medicinal product, and may be either one of completely hydrolyzed product or partially hydrolyzed product. As a partially hydrolyzed product, for example, a product having a degree of hydrolyzation ranging from 70 to 95% by mol, in particular, ranging from 80 to 90% by mol, or furthermore ranging from 85 to 90% by mol is preferably used. In addition, a degree of polymerization is not particularly limited, but preferably ranges from 100 to 3,000, and more preferably ranges from 300 to 1,000.

In the first aspect of the present invention, a solid formulation containing ingredient (A) is free from a combination of (b) polyethylene glycol and (C) polyvinyl alcohol, or in the case where a solid formulation contains a combination of (b) polyethylene glycol and (C) polyvinyl alcohol, the aforementioned ingredient (A) is isolated from the combination of (b) polyethylene glycol and (C) polyvinyl alcohol.

The term "free from ~" means that ~ does not substantially exist in a solid formulation of the present invention. Therefore, a trace amount of the aforementioned ingredient (b) and ingredient (C) may coexist within a range in which coloration of the solid formulation of the present invention can be prevented or reduced. More particularly, even if ingredient (A) is able to contact a combination of ingredient (b) and ingredient (C), the aforementioned ingredient (b) may exist in an amount of less than 1% by weight based on the total weight of the solid formulation, or may exist in an amount of less than 0.1% by weight or in an amount of less than 0.01% by weight, based on the total weight of the solid formulation. In addition, even if ingredient (A) is able to contact a combination of ingredient (b) and ingredient (C), the aforementioned ingredient (C) may exist in an amount of less than 10% by weight based on the total weight of the solid formulation, or may exist in an amount of less than 5% by weight based on the total weight of the solid formulation, or may exist in an amount of less than 1% by weight, based on the total weight of the solid formulation.

A particular embodiment of isolation in the case of isolating ingredient (A) from the combination of ingredient (b) and ingredient (C) is not particularly limited, and any options can be used as long as direct contact between ingredient (A) and the combination of ingredient (b) and ingredient (C) is inhibited.

For example, at least one isolation layer can be provided between ingredient (A), and one or both of ingredient (b) and ingredient (C).

The material of the isolation layer mentioned above is not particularly limited, as long as the material does not include both ingredient (b) and ingredient (C). For example, the material of the isolation layer may be a water-soluble polymer of a cellulose derivative such as hydroxypropyl methylcellulose (hypromellose) or hydroxypropyl cellulose, a water-soluble vinyl derivative (such as polyvinyl alcohol), or a water-soluble polymer such as polyethylene glycol or starch. In addition, as a material of the isolation layer mentioned above, a lubricant such as calcium stearate, glycerol monostearate, glyceryl palmitostearate, magnesium stearate, sodium stearyl fumarate, sucrose fatty acid ester, zinc stearate, stearic acid, or talc can also be used. In addition, a coating agent such as titanium oxide can also be used. In order to achieve assured isolation, a water-soluble polymer is preferably used, and use of hypromellose is more preferable.

Weight of the isolation layer mentioned above is not particularly limited. An amount of the isolation layer preferably ranges from 0.1 to 20% by weight, more preferably ranges from 0.5 to 15% by weight, and even more preferably ranges from 1 to 10% by weight, based on the total weight of the solid formulation.

Thickness of the isolation layer mentioned above is not particularly limited, and preferably ranges from 0.01 to 5 mm, more preferably ranges from 0.05 to 3 mm, and even more preferably ranges from 0.1 to 1 mm.

In the case of isolating ingredient (A) from a combination of ingredient (b) and ingredient (C), the amount of the aforementioned ingredient (b) and ingredient (C) contained in a solid formulation of the present invention is not limited.

In the case of ingredient (A) being isolated from a combination of ingredient (b) and ingredient (C), the amount of ingredient (b) contained in the solid formulation of the present invention can range, for example, from 0.1 to 20% by weight, and may range from 0.2 to 10% by weight, or may range from 0.3 to 5% by weight, based on the total weight of the solid formulation. In addition, the amount of ingredient (b) contained in the solid formulation of the present invention can range, for example, from 1 to 50% by weight, or may range from 3 to 45% by weight, or may range from 5 to 40% by weight, based on the total weight of the aforementioned ingredient (A).

In the case of ingredient (A) being isolated from a combination of ingredient (b) and ingredient (C), the amount of ingredient (C) contained in the solid formulation of the present invention can range, for example, from 0.1 to 20% by weight, may range from 1.0 to 10% by weight, or may range from 2.0 to 5% by weight, based on the total weight of the solid formulation. In addition, the amount of ingredient (C) contained in the solid formulation of the present invention can range, for example, from 10 to 80% by weight, may range from 20 to 75% by weight, or may range from 30 to 50% by weight, based on the total weight of the aforementioned ingredient (A).

The solid formulation preferably contains
  at least one core, and
  at least one coating layer or capsule layer enclosing at least a part of the aforementioned core, and
  the aforementioned coating layer or capsule layer is free from a combination of (b) polyethylene glycol and (C) polyvinyl alcohol, or alternatively,
  in the case of the aforementioned coating layer or capsule layer containing a combination of (b) polyethylene glycol and (C) polyvinyl alcohol, at least one isolation layer is provided between the core and the coating layer or capsule layer.

Only one core may be present in the solid formulation of the present invention, or two or more cores may be present.

The core preferably contains ingredient (A). The form of the core is not particularly limited, and the core may be in the form of a mixture of simple powders, granules or the like. On the other hand, in the case of the solid formulation of the present invention being in the form of a film-coated tablet, the core mentioned above can be an uncoated tablet before film-coating. In addition, in the case of the solid formulation of the present invention being in the form of a capsule tablet, the aforementioned core can form a granule to be capsulated.

The aforementioned core preferably contains an inert carrier together with ingredient (A). The inert carrier mentioned above preferably contains at least one additive selected from the group consisting of a filler, a disintegrant, a binder, a lubricant, and a fluidizer.

As the filler, at least one selected from the group consisting of sugars, sugar alcohols, inorganic fillers and crystalline cellulose is preferable. Examples of sugars include, for example, lactose (lactose hydrate, anhydrous lactose), saccharose, sucrose, fructose, fructooligosaccharides, glucose, maltose, reduced maltose, powder sugar, powdered candy, reduced lactose, and the like. Examples of sugar alcohols include, for example, erythritol, sorbitol, maltitol, xylitol, mannitol, and the like. Examples of inorganic fillers include, for example, anhydrous calcium hydrogen phosphate, anhydrous calcium phosphate, precipitated calcium carbonate, calcium silicate, and the like. A combination of two or more types among these may be used. Mannitol, crystalline cellulose, or a mixture thereof is preferable. An amount of the filler in the core mentioned above is not particularly limited, usually ranges from 60 to 99% by weight, preferably ranges from 70 to 95% by weight, and more preferably ranges from 80 to 90% by weight based on the total weight of the core.

As the disintegrant, at least one selected from the group consisting of natural starches, starch derivatives, crospovidone, carboxymethyl cellulose, carboxymethyl cellulose calcium, low-substituted hydroxypropyl cellulose and carmellose is preferable. For example, examples of natural starches include corn starch, potato starch, rice starch, wheat starch and the like. Examples of starch derivatives include hydroxypropyl starch obtained by processing the natural starch, and the like. A combination of two or more types among these may be used. Carmellose is preferable, croscarmellose is more preferable, and croscarmellose sodium is even more preferable. An amount of the disintegrant in the aforementioned core is not particularly limited, but usually ranges from 0.1 to 20% by weight, preferably ranges from 1.0 to 10% by weight, and more preferably ranges from 2.0 to 5% by weight based on the total weight of the core.

Examples of the binder include, for example, hydroxypropyl cellulose, polyvinyl alcohol, povidone (polyvinylpyrrolidone), hypromellose (hydroxypropyl methylcellulose), agar, gelatin and the like. A combination of two or more types among these may be used. Hypromellose is preferable. An amount of the binder in the aforementioned core is not particularly limited, but usually ranges from 0.1 to 20% by weight, preferably ranges from 1.0 to 10% by weight, and more preferably ranges from 2.0 to 5% by weight.

Examples of the lubricant include, for example, calcium stearate, glycerol monostearate, glyceryl palmitostearate, magnesium stearate, sodium stearyl fumarate, sucrose fatty acid ester, zinc stearate, stearic acid, talc, and the like. A combination of two or more types among these may be used. Magnesium stearate is preferable. An amount of the lubricant in the core is not particularly limited, but usually ranges from 0.1 to 20% by weight, preferably ranges from 0.5 to 10% by weight, and more preferably ranges from 1.0 to 5% by weight based on the total weight of the core.

Examples of fluidizer include, for example, light anhydrous silicic acid, hydrated silicon dioxide, and the like. A combination of two or more types among these may be used. Light anhydrous silicic acid is preferable. An amount of the fluidizer in the core is not particularly limited, but usually ranges from 0.01 to 10% by weight, preferably ranges from 0.1 to 5% by weight, and more preferably ranges from 0.5 to 3% by weight based on the total weight of the core.

In order to provide good administration ability in the oral cavity, a sweetener and/or a flavoring agent or a perfuming agent may preferably be added to the aforementioned core. Examples of the sweetener include, for example, dipotassium glycyrrhizinate, saccharin sodium, saccharin, stevia, aspartame, sucralose, thaumatin, acesulfame-K, neotame, and the like. Examples of the flavoring agent or the perfuming agent include, for example, citrus flavors of lemon, orange, grapefruit, and the like, peppermint, spearmint, menthol, pine, cherry, fruit, yogurt, coffee, and the like.

In the core mentioned above, non-toxic and inert additives commonly used in the formulation field can be added within the range which does not affect the effects of the present invention. Examples of the additive used include, for example, a surfactant, an organic acid, a colorant, and the like.

A method for producing the core mentioned above is not particularly limited. For example, in the case of the core mentioned above being in the form of a granule, the core can be manufactured by means of a fluid bed granulator represented by a flow coater (manufactured by Freund Corp.), a GPCG (Glatt Powder Coater Granulator), a WSG (Wirbel Schicht Granulator), a multiplex (GLATT/manufactured by Powrex Corporation), or the like, or by means of a stirring granulator represented by a vertical granulator (manufactured by Powrex Corporation), or the like.

In addition, in the case of the core mentioned above being in the form of an uncoated tablet, a wet granulation tableting method in which the granules manufactured by means of the aforementioned manufacturing method are molded, a direct tableting method in which various raw materials are suitably mixed, and the mixed powder is molded, or a dry granulation tableting method can be used. As the molding method mentioned above, a compression molding method using a rotary tableting machine or the like is preferable from a commercial point of view. The uncoated tablet can also be molded by means of an external lubricating method. In this case, tableting is carried out after mixing the ingredients other than a lubricant, while spraying the lubricant on a die-punch, or alternatively, tableting is carried out after previously mixing a part of the lubricant with the ingredients other than a lubricant, by spraying the remaining lubricant on a die-punch. In addition, the uncoated tablet can also be manufactured by means of a special tablet press such as a tablet press for nucleated tablets, a two-layer tablet press, or a three-layer tablet press.

In the case of the core mentioned above being an uncoated tablet, in order to maintain a good balance between disintegration time and hardness, a suitable tableting pressure is preferably selected during production of the uncoated tablets. The tableting pressure is normally 2 kN (about 200 kgf) or more, preferably 4 kN (about 400 kgf) or more, and more preferably 6 kN (about 600 kgf) or more.

In the solid formulation of the present invention according to the aforementioned embodiment, only one coating layer or capsule layer mentioned above enclosing the core mentioned above may be present, or two or more coating layers or capsule layers may be present. Here, "enclosing" means that the coating layer or capsule layer encloses the core, and does not necessarily contact the core. For example, at least one isolating layer may be present between the core and the coating layer or capsule layer. In this case, the core does not directly contact the coating layer or capsule layer. On the other hand, the core may directly contact the coating layer or capsule layer. In this case, the coating layer or capsule layer contains neither ingredient (b) nor ingredient (C). On the other hand, even if the core directly contacts the coating layer or capsule layer, the coating layer or capsule layer can contain either one of ingredient (b) or ingredient (C).

The weight of the isolation layer mentioned above is not particularly limited, and preferably ranges from 0.1 to 20% by weight, more preferably ranges from 0.5 to 15% by weight, and even more preferably ranges from 1 to 10% by weight based on the total weight of the solid formulation.

The thickness of the isolation layer mentioned above is not particularly limited, and preferably ranges from 0.01 to 5 mm, more preferably ranges from 0.05 to 3 mm, and even more preferably ranges from 0.1 to 1 mm.

The coating layer or capsule layer mentioned above can be present in a ratio ranging from 0.1 to 20% by weight, preferably ranging from 0.5 to 15% by weight and further more ranging from 1 to 10% by weight based on the total weight of the solid formulation.

The coating layer or capsule layer mentioned above may include a small amount of ingredient (A). In this case, an amount of the aforementioned ingredient (A) included therein is preferably 10% by weight or less, more preferably 5% by weight or less, more preferably 1% by weight or less, and even more preferably 0.1% by weight or less, based on the total weight of the aforementioned layer. In particular, preferably, the coating layer or capsule layer mentioned above does not contain ingredient (A).

The coating layer or capsule layer mentioned above can contain ingredient (b) in an amount ranging from 0.1 to 50% by weight based on the total weight of the coating layer or capsule layer. The amount may range from 0.1 to 40% by weight, or may range from 1 to 30% by weight.

The coating layer or capsule layer mentioned above can contain ingredient (C) in an amount ranging from 50 to 90% by weight based on the total weight of the coating layer or capsule layer. The amount may range from 50 to 80% by weight, or may range from 50 to 70% by weight.

The coating layer or capsule layer preferably further contains at least one selected from the group consisting of a water-soluble polymer other than polyethylene glycol and polyvinyl alcohol, a colorant, a lubricant, and wax.

Examples of the water-soluble polymer mentioned above include, for example, cellulose-based derivatives such as hypromellose (hydroxypropyl methylcellulose), methyl cellulose, hydroxypropyl cellulose, carboxymethyl cellulose sodium, hydroxyethyl methylcellulose, hydroxypropyl methylcellulose phthalate, and hydroxypropyl methylcellulose acetate succinate, starches such as starch and pullulan, water-soluble vinyl derivatives such as polyvinyl pyrrolidone, sodium alginate, gum arabic powder, gelatin and the like. Hypromellose, hydroxypropyl cellulose, water-soluble vinyl derivatives, and starches are preferable. Hypromellose, hydroxypropyl cellulose, and water-soluble vinyl derivatives are more preferable. Hypromellose and hydroxypropyl cellulose are most preferable. In addition, a mixture of a disintegrant auxiliary agent and an enteric polymer or a water-insoluble polymer may be contained, in addition to the water-soluble polymer. Examples of the enteric polymer include, for example, enteric cellulose esters such as cellulose acetate propionate, hydroxypropyl methylcellulose acetate succinate (for example, trade name: Shin-Et-suAQOAT, manufactured by Shin-Etsu Chemical Co., Ltd.), hydroxypropyl methylcellulose phthalate, carboxymethyl ethylcellulose, and cellulose acetate phthalate, enteric acrylic acid-based copolymers such as methacrylic acid copolymer L (for example, trade name: Eudragit L, manufactured by Evonik Degussa Japan), methacrylic acid copolymer LD (for example, trade name: Eudragit L 30D-55, manufactured by Evonik Degussa Japan, tradename: POLYQUID PA 30, POLYQUID PA 30-S, manufactured by Sanyo Chemical Industries, Ltd., trade name: Kollicoat MAE 30DP, manufactured by BASF), and methacrylic acid copolymer S (for example, trade name: Eudragit S, Eudragit S 100, Eudragit FS 30D, manufactured by Evonik Degussa Japan), and the like. These polymers may be used in a mixture of two or more types.

The water-soluble polymer is preferably hydroxypropyl methylcellulose. An amount of the water-soluble polymer mentioned above in the coating layer or capsule layer mentioned above is not particularly limited. The amount usually ranges from 50 to 99% by weight, preferably ranges from 60 to 95% by weight and more preferably ranges from 70 to 90% by weight based on the total weight of the coating layer or capsule layer.

The colorant mentioned above is preferably selected from the group consisting of titanium oxide, iron oxide, zinc oxide, tar pigments, and lake pigments.

Examples of iron oxide include, for example, black iron oxide, red ferric oxide, yellow ferric oxide, and the like. Examples of tar pigments include, for example, water-soluble edible tar pigments such as food yellow No. 5 and food blue No. 2. Examples of lake pigments include, for example, yellow No. 5 aluminum lake, and the like. A combination of two or more types among these may be used. Titanium oxide is preferable. The amount of the colorant in the coating layer or capsule layer mentioned above is not particularly limited, but usually ranges from 1 to 20% by weight, preferably ranges from 3 to 15% by weight, and more preferably ranges from 5 to 10% by weight, based on the total weight of the coating layer or capsule layer.

Examples of the lubricant include, for example, calcium stearate, glycerol monostearate, glyceryl palmitostearate, magnesium stearate, sodium stearyl fumarate, sucrose fatty acid ester, zinc stearate, stearic acid, talc, and the like. A combination of two or more types among these may be used. Talc is preferable.

An amount of the lubricant in the coating layer and capsule layer is not particularly limited, but usually ranges from 0.1 to 20% by weight, preferably ranges from 0.5 to 15% by weight, and more preferably ranges from 1.0 to 10% by weight, based on the total weight of the coating layer or capsule layer.

Examples of the wax include, for example, carnauba wax, beeswax, stearic acid and the like. A combination of two or more types among these may be used. Carnauba wax is preferable. An amount of the wax in the coating layer or capsule layer is not particularly limited, but usually ranges from 0.01 to 10% by weight, preferably ranges from 0.05 to 1% by weight, and more preferably ranges from 0.05 to 0.1% by weight, based on the total weight of the coating layer or capsule layer.

The coating layer or capsule layer mentioned above can contain a plasticizer other than ingredient (b). The types of the plasticizer are not particularly limited. For example, (B) at least one type selected from the group consisting of propylene glycol, glycerol, glyceryl triacetate, triethyl acetyl citrate, dibutyl sebacate, diethyl phthalate, castor oil, a copolymer of propylene oxide and ethylene oxide, triacetin, triethyl citrate, and a mixture thereof (hereinafter, simply referred to as "ingredient (B)" in some cases) can be used.

In order to further prevent or reduce decomposition of ingredient (A) in the solid formulation of the present invention over time, in the case of the core mentioned above contacting the coating layer or capsule layer mentioned above, the coating layer or capsule layer mentioned above is free from ingredient (B), or alternatively, even if the coating layer or capsule layer mentioned above contains ingredient (B), the amount thereof is preferably 0.9% by weight or less, more preferably 0.8% by weight or less, even more preferably 0.6% by weight or less, even more preferably 0.4% by weight or less, and in particular, preferably 0.3% by weight or less, based on the total weight of the solid formulation. More particularly, in the case of the aforementioned core contacting the aforementioned coating layer or capsule layer, the coating layer or capsule layer can contain the aforementioned ingredient (B), for example, in an amount ranging from 0.1 to 40% by weight based on the total weight of the coating layer or capsule layer, and the amount thereof preferably ranges from 1 to 35% by weight, and more preferably ranges from 5 to 10% by weight.

The coating layer or capsule layer can contain a plasticizer other than the ingredient (B) and ingredient (b) mentioned above. Examples of the plasticizer mentioned above include, for example, polysorbates such as polysorbate 20, polysorbate 40, polysorbate 60, and polysorbate 80, and the like. The amount of the aforementioned plasticizer ranges, for example, from 1 to 20% by weight, preferably ranges from 3 to 15% by weight, and more preferably ranges from 5 to 10% by weight, based on the coating layer or capsule layer mentioned above.

A method for forming the coating layer or capsule layer is not particularly limited. In the case of the core directly contacting the coating layer or capsule layer, the coating layer or capsule layer may be directly formed on the surface of the core by means of a coating machine represented by HICOATER, new HICOATER, AQUA COATER (manufactured by Freund Corp.), DOREA COATER, POWREX COATER (manufactured by Powrex Corporation), or the like, a sugar-coating pan, a Wurster type coating machine, or the like. On the other hand, in the case of the core directly non-contacting the coating layer or capsule layer, at least one isolation layer mentioned above may be formed on the surface of the core by means of the aforementioned coating machine, and the coating layer or capsule layer can be formed on the surface of the isolation layer by means of the aforementioned coating machine. In addition, after forming the coating layer or capsule layer, an intraoral disintegration property can also be improved by humidification or the like.

The formation of the coating layer or capsule layer and the formation of the isolation layer are preferably carried out using an aqueous coating liquid. The aqueous coating liquid means an aqueous dispersion or solution of the constitutional ingredients of the coating layer or capsule layer or those of the isolation layer, and means a coating liquid containing of water or a mixed solution of water/water-soluble organic solvent, as a medium.

The water amount in the aqueous coating liquid is suitably determined in accordance with types and blending amounts of the ingredients and the amount of the water-soluble organic solvent added. The preferable water amount ranges, for example, from 5 to 1,000 parts by weight, preferably ranges from 7 to 100 parts by weight, and more preferably ranges from 8 to 50 parts by weight based on one part by weight of the constitutional ingredients of the isolation layer or the coating layer or capsule layer.

Examples of the water-soluble organic solvent which may be added to the aqueous coating liquid include, for example, methanol, ethanol, propyl alcohol, isopropyl alcohol, acetone, methyl ethyl ketone, dioxane, tetrahydrofuran, acetonitrile, and the like. In particular, ethanol is preferable. The amount of the water-soluble organic solvent added is determined in accordance with the types and blending amount of the ingredients, preferably ranges from 0 to 8.0 parts by weight, more preferably ranges from 0 to 2.4 parts by weight, even more preferably ranges from 0 to 1.3 parts by weight, and even more preferably ranges from 0 to 0.4 parts by weight based on one part by weight of water. In particular, the medium is preferably only water without adding a water-soluble organic solvent. Here, the medium which is only water means that only water is substantially used, and contamination of a small amount (for example 0.03 parts by weight or less based on one part by weight of water) of an organic solvent is acceptable.

The temperature of the exhaust gas temperature of the coating machine during the coating step is preferably controlled so that the temperature is higher than 30° C., but lower than 60° C. in the present invention. The coating step used herein means a step of applying the coating liquid on the core by means of a spray or the like, and during the step, ventilation is carried out. The exhaust gas temperature mentioned above is preferably 32° C. or higher, but 55° C. or lower, and more preferably 35° C. or higher, but 45° C. or lower. When the exhaust gas temperature mentioned above is 30° C. or lower, or alternatively 60° C. or higher, separation of a coating film may easily occur, roughness of the coating film may be increased, and therefore, a good coating film may not be formed in some cases.

Alternatively, in the present invention, the product temperature during the coating step is preferably controlled so that the product temperature is higher than 20° C., but lower than 56° C. Here, the product temperature during the coating step is the temperature of the core during the coating step. The product temperature can be measured by means of an infrared thermometer. The product temperature mentioned above is preferably 25° C. or higher, but 50° C. or lower, and more preferably 35° C. or higher, but 45° C. or lower. If the aforementioned product temperature is 20° C. or lower or 56° C. or higher, separation of the coating film may easily occur, roughness of the coating film may be increased, and a good coating film may not be formed in some cases.

During controlling of the exhaust gas temperature or the product temperature, the adjustment of the exhaust gas temperature or the product temperature can be carried out by adjusting, for example, the charge gas temperature, the amount of the charge gas, or the addition rate of the coating liquid (spraying rate and the like). In particular, controlling of the charge gas temperature is preferably carried out.

The application of the coating liquid may be carried out by pouring-and-adding or spraying, and spraying is preferable. In the case where, for example, 1 kg of uncoated tablets (250 mg/tablet) are subjected to spray coating by means of a ventilation type coating machine such as HICOATER (manufactured by Freund Corp.) or the like, the blast temperature may be set based on the exhaust temperature criteria, and the spray coating can be carried out in an air volume ranging from 1.5 to 3.5 m$^3$/min at a spray rate ranging from 5 to 50 g/min.

The particular structure of the solid formulation of the present invention is not particularly limited. For example, the solid formulation may be in the form of fine granules, granules, capsules, or tablets. In the case of tablets, from one to two dividing lines for making division of the tablet easy may be provided. The shape of the tablet is not particularly limited, and may be, for example, round, oval (any oblong except for perfect circle; oval, egg-shaped, elliptical cylinder shape, old gold coin-shaped, or the like), diamond-shaped, triangle, or the like. The solid formulation may be in the form of so-called specially shaped tablets. In the case of providing a dividing line, the dividing line shape may be any of flat groove type, U-shaped groove type, or V-groove type. In the case of the tablet being in an oval shape, the dividing line can be preferably formed along the minor axis of the tablet.

The solid formulation of the present invention is preferably in the form of a tablet or a capsule. In the case of a tablet, a film-coating agent is preferable.

The size of the tablet mentioned above not particularly limited. In the case of the tablet being in a general-column shape, the diameter of the column preferably ranges from 5 to 11 mm, more preferably ranges from 5 to 10 mm, and even more preferably ranges from 5 to 9 mm. In the case of the tablet being a specially shaped tablet, the maximum length of the specially shaped tablet can range from 5 to 11 mm, more preferably ranges from 5 to 10 mm, and even more preferably ranges from 5 to 9 mm.

A second aspect of the present invention relates to a method for preventing or reducing coloration of a solid formulation containing a certain benzothia(dia)zepine derivative, characterized in that
  a combination of (b) polyethylene glycol and (C) polyvinyl alcohol is not added to the aforementioned solid formulation, or alternatively,
  in the case of adding a combination of (b) polyethylene glycol and (C) polyvinyl alcohol to the aforementioned solid formulation, the aforementioned benzothia(dia)zepine derivative is isolated from the combination of (b) polyethylene glycol and (C) polyvinyl alcohol.

The aforementioned benzothia(dia)zepine derivative is identical to the aforementioned ingredient (A) in the first aspect of the present invention. Therefore, hereinafter, it is referred to as ingredient (A).

The aforementioned polyethylene glycol (b) is identical to the aforementioned ingredient (b) in the first aspect of the present invention. Therefore, hereinafter, it is referred to as ingredient (b).

The aforementioned polyvinyl alcohol (C) is identical to the aforementioned ingredient (C) in the first aspect of the present invention. Therefore, hereinafter, it is referred to as ingredient (C).

In the case of the aforementioned ingredient (A) being isolated from the combination of the aforementioned ingredient (b) and ingredient (C), the amount of the aforementioned ingredient (b) and/or ingredient (C) contained in the solid formulation of the present invention is not limited.

On the other hand, in the case of the aforementioned ingredient (A) not being isolated from the combination of the aforementioned ingredient (b) and ingredient (C), that is, in the case of the aforementioned ingredient (A) being able to contact the combination of the aforementioned ingredient (b) and ingredient (C), the solid formulation is free from a combination of ingredient (b) and ingredient (C). Here, "free from ~" means that ~ is not substantially included in the solid formulation of the present invention. A trace amount of ingredient (b) and ingredient (C) may coexist within such a range that coloration of the solid formulation of the present invention is prevented or reduced. More particularly, even if ingredient (A) is able to contact the combination of ingredient (b) and ingredient (C), the aforementioned ingredient (b) may exist in an amount of less than 1.0% by weight based on the total weight of the solid formulation. In addition, less than 0.1% by weight, or less than 0.01% by weight of ingredient (b) may exist. In addition, even if ingredient (A) is able to contact the combination of ingredient (b) and ingredient (C), the aforementioned ingredient (C) may exist in an amount of less than 10% by weight based on the total weight of the solid formulation, or less than 5% by weight of ingredient (C) may exist, or less than 1% by weight of ingredient (C) may exist.

The explanation described above for the first aspect of the present invention can be applied to the solid formulation in the second aspect of the present invention. Therefore, for example, the amount of ingredient (A) in the solid formulation is not particularly limited, but the amount can range from 0.01 to 50% by weight, preferably ranges from 0.05 to 40% by weight, more preferably ranges from 0.1 to 30% by weight, even more preferably ranges from 0.2 to 20% by weight, even more preferably ranges from 0.5 to 10% by weight, and in particular, preferably ranges from 0.8 to 5% by weight, based on the total weight of the solid formulation.

In addition, the amount of the ingredient (A) mentioned above in the solid formulation is not particularly limited, can range from 0.1 to 100 mg, preferably ranges from 0.3 to 75 mg, more preferably ranges from 0.5 to 50 mg, even more preferably ranges from 0.8 to 30 mg, and in particular, preferably ranges from 1 to 20 mg.

In accordance with the present invention, in a solid formulation containing ingredient (A), the derivative mentioned above can be stabilized therein. Therefore, a solid formulation containing stabilized ingredient (A) can be provided.

Ingredient (A) in the solid formulation mentioned above is stable over time even under an atmosphere of high temperature and/or high humidity. Therefore, even if the solid formulation of the present invention is present under an atmosphere of high temperature and/or high humidity, occurrence of coloration (in particular, red coloration) of the solid formulation due to destabilization of the ingredient (A) mentioned above can be prevented or reduced. In particular, in accordance with the present invention, the solid formulation can be stable in a well-closed environment.

Therefore, in accordance with the present invention, the solid formulation can be stored for a long period of time, and the pharmaceutical effects of the ingredient (A) mentioned above contained in the solid formulation can be maintained. In particular, in accordance with the present invention, the solid formulation containing the ingredient (A) mentioned above can be stable even under an atmosphere of high temperature and high humidity in the summer season.

INDUSTRIAL APPLICABILITY

The present invention can provide a stabilized solid formulation containing a specified benzothia(dia)zepine derivative. The specific benzothia(dia)zepine derivatives mentioned above can function as an IBAT inhibitor, and for this reason, the solid formulations according to the present invention are useful for a long period of time in the treatment of dyslipidemic conditions and disorders such as hyperlipidemia, hypertriglyceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL), as well as in the treatment of functional constipation or constipation-predominant irritable bowel syndrome.

EXAMPLES

Hereinafter, the present invention is described in detail with reference to Examples and Comparative Examples. It should be understood that the present invention is not limited to these Examples.

Reference Examples 1 to 9

1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiazepine (Elobixibat) and an additive shown in Table 1 were mixed so that they have a volume ratio of 1:1 based on visual quantities, and thereby, the mixtures according to Reference Examples 3 to 9 were obtained. In Reference Examples 8 and 9, two types of additives shown in Table 1 were mixed in a weight ratio of 1:1, and the obtained mixture was further mixed with Elobixibat so that they had a volume ratio of 1:0.5 based on visual quantities. The mixture of each of Reference Examples 3 to 9, only Elobixibat as Reference Example 1, and only Macrogol (polyethylene glycol) 6000 as Reference Example 2 were independently stored in an aluminum bag as an airtight container for 2 weeks under the conditions of 60° C. and 75% relative humidity. After storage, the presence or absence of coloration of the materials of Reference Examples 1 and 2 and the mixtures according to Reference Examples 3 to 9 was visually observed. The results are shown in Table 1.

TABLE 1

| | Mixture | | Coloration after storage Before storage → after storage |
|---|---|---|---|
| | Drug substance | Additive(s) | |
| Reference Example 1 | Elobixibat | — | — | Not observed white → white |
| Reference Example 2 | — | Macrogol 6000 | — | Not observed White → white |
| Reference Example 3 | Elobixibat | Polyvinyl alcohol partial-saponification product | — | Not observed White → white |
| Reference Example 4 | Elobixibat | Hypromellose | — | Not observed White → white |
| Reference Example 5 | Elobixibat | Talc | — | Not observed White → white |
| Reference Example 6 | Elobixibat | Titanium oxide | — | Not observed White → white |
| Reference Example 7 | Elobixibat | Macrogol 6000 | — | Observed White → pale yellow |
| Reference Example 8 | Elobixibat | Macrogol 6000 | Titanium oxide | Observed White → pale yellow |
| Reference Example 9 | Elobixibat | Polyvinyl alcohol partial-saponification product | Macrogol 6000 | Observed White → pale pink |

As is clear from Table 1, in Elobixibat alone (Reference Example 1) or Macrogol 6000 alone (Reference Example 2), coloration was not observed. In addition, in the mixture of Elobixibat with polyvinyl alcohol partial-saponification product (Reference Example 3), Hypromellose (Reference Example 4), Talc (Reference Example 5) or titanium oxide (Reference Example 6), coloration was not observed.

On the other hand, in the ternary system mixture of Elobixibat, polyvinyl alcohol partial-saponification product, and Macrogol 6000 (Reference Example 9), coloration to pale pink occurred.

In the binary system mixture of Elobixibat and Macrogol 6000 (Reference Example 7) and the ternary system mixture of Elobixibat, Macrogol 6000 and titanium oxide (Reference Example 8), slight coloration to pale yellow was observed, but was not light pink as observed in Reference Example 9.

Therefore, it can be seen that coloration to red in an Elobixibat-containing formulation is caused by contacting Elobixibat with a combination of polyethylene glycol and polyvinyl alcohol.

Examples 1 to 4 and Comparative Examples 1 and 2

Crystalline cellulose (filler), D-mannitol (filler), Hypromellose (binder), croscarmellose sodium (disintegrant), light anhydrous silicic acid (fluidizer), magnesium stearate (lubricant), and 1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiazepine (Elobixibat) were formulated into tablets in accordance with a conventional method (mixing in a bag or mixing by means of a rotatory mixer, and tableting by means of a rotary tableting machine). Thereby, uncoated tablets (weight of uncoated tablet: 110 mg or 320 mg) containing 5% by weight of Elobixibat (drug substance) were obtained.

Macrogol 6000 (plasticizer), and Hypromellose (coating agent) or polyvinyl alcohol partial-saponification product (coating agent) were added to purified water, and mixed well until the mixture was dissolved. After the mixture was dissolved, titanium oxide (colorant) was added thereto, and mixed well to disperse it therein. The obtained mixture liquid was used as a film coating liquid. The compositions of the film coatings according to Examples 1 to 4 and Comparative Examples 1 and 2 are shown in Table 2.

The aforementioned film coating liquid was sprayed onto the aforementioned uncoated tablets by means of a pan-type coating machine. Thereby, the film coating tablets according to Examples 1 and 3, Comparative Example 1 and Comparative Example 2 were obtained.

On the other hand, Hypromellose was added to purified water and mixed well until it was dissolved. Thereby, the solution was used as a shielding coating liquid. The shielding coating liquid was sprayed onto the uncoated tablets by means of a pan-type coating machine, and shielding coating was carried out. Subsequently, the aforementioned film coating liquid containing polyvinyl alcohol was sprayed onto the tablets which had been subjected to shielding coating. Thereby, the film coating tablets according to Example 2 and Example 4, in which a shielding coating layer (isolation layer) was provided, were obtained.

The obtained film coating tablets in accordance with each of Examples 1 to 4 and Comparative Examples 1 and 2 were stored in an aluminum bag as an airtight container for 2 weeks under the conditions of 60° C. and 75% relative humidity. The outer appearance of the tablets before and after storage was observed, and the coloration state thereof was evaluated. The results are shown in Table 2.

TABLE 2

| Example/Comparative Example | | | Example 1 | Example 2 | Example 3 | Example 4 | Comparative Example 1 | Comparative Example 2 |
|---|---|---|---|---|---|---|---|---|
| Weight of uncoated tablets | | [mg/tablet] | 110 | 110 | 320 | 320 | 110 | 320 |
| Total weight of shielding coating | | | — | 3.2 | — | 18.2 | — | — |
| Total weight of film coating | | | 2.1 | 4.2 | 8.1 | 17.1 | 4.5 | 16.7 |
| Composition of film coating part | Hypromellose | [parts by weight] | 63 | — | 63 | — | — | — |
| | polyvinyl alcohol partial-saponification product | | — | 63 | — | 63 | 63 | 63 |
| | Macrogol6000 | | 31 | 31 | 31 | 31 | 31 | 31 |
| | Titanium oxide | | 6 | 6 | 6 | 6 | 6 | 6 |
| Coloration after storage for 2 weeks Before storage → after storage | | | — | Not observed White → white | Not observed Cream color → cream color | Not observed White → white | Not observed Cream color → cream color | Observed White → slightly pale pink | Observed White → slightly pale pink |

As is clear from Table 2, in Comparative Example 1 and Comparative Example 2, in which the film coating contained a combination of polyvinyl alcohol partial-saponification product and Macrogol 6000, and the aforementioned film coating contacted uncoated tablets, the surface of the tablets was colored to pale pink.

On the other hand, in Example 1 and Example 3 in which the film coating did not contain a combination of polyvinyl alcohol partial-saponification product and Macrogol 6000, and the aforementioned coating film contacted the uncoated tablets, no red coloration at the surface of the tablets was observed. In addition, even in the case of the film coating containing both polyvinyl alcohol partial-saponification product and Macrogol 6000, in Example 2 and Example 4, in which a shielding coating layer was provided between the uncoated tablets and the film coating, controlling of coloration could be carried out.

What is claimed is:

1. A solid formulation comprising:
   (A) 1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiazepine, or a pharmaceutically acceptable salt, solvate, or solvate of such a salt;
   one core, wherein the core is a homogenous mixture comprising ingredient (A);
   one coating layer or capsule layer enclosing at least a part of the core, wherein the coating layer or capsule layer comprises (b) polyethylene glycol present in an amount ranging from about 0.1 to about 50% by weight based on the total weight of the coating layer or capsule layer;
   wherein the solid formulation does not comprise (C) polyvinyl alcohol.

2. The solid formulation according to claim 1, wherein the amount of the ingredient (A) ranges from 0.01 to 50% by weight based on the total weight of the solid formulation.

3. The solid formulation according to claim 1, wherein the amount of the ingredient (A) ranges from 1 to 20 mg.

4. The solid formulation according to claim 1, wherein the average molecular weight of ingredient (b) is 200 to 20,000.

5. The solid formulation of claim 4, wherein the average molecular weight of ingredient (b) is 300 to 10,000.

6. The solid formulation according to claim 1, wherein the coating layer or capsule layer is present in a ratio ranging from 1 to 20% by weight based on the total weight of the solid formulation.

7. The solid formulation according to claim 1, wherein the coating layer or capsule layer further comprises at least one selected from the group consisting of a water-soluble polymer other than polyethylene glycol or polyvinyl alcohol, a colorant, a lubricant, and a wax.

8. The solid formulation according to claim 7, wherein the water-soluble polymer is hydroxypropyl methylcellulose.

9. The solid formulation according to claim 7, wherein the colorant is selected from the group consisting of titanium oxide, iron oxide, zinc oxide, tar pigment, and lake pigment.

10. The solid formulation according claim 7, wherein the wax is carnauba wax.

11. The solid formulation according to claim 1, wherein the core further comprises at least one additive selected from the group consisting of a filler, a disintegrant, a binder, a lubricant, and a fluidizer.

12. The solid formulation according to claim 11, wherein the filler is selected from the group consisting of mannitol, crystalline cellulose, or a combination thereof.

13. The solid formulation according to claim 11, wherein the solid formulation comprises the filler in an amount ranging from 60% to 99% by weight based on the total weight of the solid formulation.

14. The solid formulation according to claim 11, wherein the disintegrant is croscarmellose sodium.

15. The solid formulation according to claim 11, wherein the binder is hydroxypropyl methylcellulose.

16. The solid formulation according to claim 11, wherein the lubricant is magnesium stearate.

17. The solid formulation according to claim 1, wherein the solid formulation is in the form of a tablet having a diameter ranging from 5 to 11 mm.

18. A method of treating constipation in a warm-blooded animal comprising administering the solid formulation according to claim 1.

19. The method according to claim 18, wherein the constipation is functional constipation or constipation-predominant irritable bowel syndrome.

20. The method according to claim 18, wherein the warm-blooded animal is a human.

* * * * *